US006593362B2

(12) United States Patent
Steiner et al.

(10) Patent No.: US 6,593,362 B2
(45) Date of Patent: Jul. 15, 2003

(54) NON-PEPTIDIC CYCLOPHILIN BINDING COMPOUNDS AND THEIR USE

(75) Inventors: Joseph P. Steiner, Mt. Airy, MD (US); Gregory S. Hamilton, Catonsville, MD (US)

(73) Assignee: Guilford Pharmaceuticals Inc., Baltimore, MD (US)

( * ) Notice: Subject to any disclaimer, the term of this patent is extended or adjusted under 35 U.S.C. 154(b) by 0 days.

(21) Appl. No.: 09/860,756

(22) Filed: May 21, 2001

(65) Prior Publication Data

US 2003/0055009 A1 Mar. 20, 2003

(51) Int. Cl.[7] .................. A61K 31/27; A61K 31/275; A61K 31/175; A61K 31/17
(52) U.S. Cl. .................. 514/477; 514/478; 514/479; 514/482; 514/491; 514/589; 514/590; 514/596
(58) Field of Search .................. 514/477, 478, 514/479, 482, 491, 589, 590, 596

(56) References Cited

U.S. PATENT DOCUMENTS

| | | | |
|---|---|---|---|
| 4,384,996 A | 5/1983 | Bollinger et al. |
| 4,681,871 A | 7/1987 | Teschemacher et al. |
| 4,703,033 A | 10/1987 | Seebach |
| 4,764,503 A | 8/1988 | Wenger |
| 4,885,276 A | 12/1989 | Witzel |
| 4,914,188 A | 4/1990 | Dumont et al. |
| 4,957,903 A | 9/1990 | Ranby |
| 5,019,646 A | 5/1991 | Furcht et al. |
| 5,100,899 A | 3/1992 | Calne |
| 5,116,816 A | 5/1992 | Dreyfuss et al. |
| 5,122,511 A | 6/1992 | Patchett et al. |
| 5,134,121 A | 7/1992 | Mobley et al. |
| 5,284,826 A | 2/1994 | Eberle et al. |
| 5,321,009 A | 6/1994 | Baeder et al. |
| 5,330,993 A | 7/1994 | Armistead et al. |
| 5,449,612 A | 9/1995 | Lepargneur et al. |
| 5,462,927 A | 10/1995 | Mureau et al. |
| 5,464,820 A | 11/1995 | Burton et al. |
| 5,478,810 A | 12/1995 | Stuber et al. |
| 5,545,719 A | 8/1996 | Shashoua |
| 5,614,547 A | 3/1997 | Hamilton et al. |
| 5,696,135 A | 12/1997 | Steiner et al. |
| 5,721,256 A | 2/1998 | Hamilton et al. |
| 5,786,378 A | 7/1998 | Hamilton et al. |
| 5,795,908 A | 8/1998 | Hamilton et al. |
| 5,798,355 A | 8/1998 | Steiner et al. |

(List continued on next page.)

FOREIGN PATENT DOCUMENTS

| | | |
|---|---|---|
| EP | 0 053 029 | 6/1982 |
| WO | WO 88/06451 | 9/1988 |
| WO | WO 92/04370 | 3/1992 |
| WO | WO 92/19254 | 11/1992 |
| WO | WO 96/40633 | 12/1996 |
| WO | WO 97/18828 | 5/1997 |
| WO | WO 97/36869 | 10/1997 |
| WO | WO 98/25950 | 6/1998 |
| WO | WO 01/17953 | * 3/2001 |

OTHER PUBLICATIONS

Baetge, E. Edward, et al., "Neurite Outgrowth in PC12 Cells Deficient in GAP–43," *Neuron*, vol. 6, 21–30, Jan. 1991.
Barinaga, M., "Neurotrophic Factors Enter The Clinic," *Science* 264:772–774.

(List continued on next page.)

*Primary Examiner*—Sreeni Padmanabhan
*Assistant Examiner*—San-ming Hui
(74) *Attorney, Agent, or Firm*—Howrey Simon Arnold & White, LLP

(57) ABSTRACT

This invention relates to pharmaceutical compositions and methods of using non-peptidic cyclophilin-binding compounds in medical conditions involving breakdown of mitochondrial energy metabolism induced by calcium overload, in treating alopecia and promoting hair growth, in treating infections with filarial and helminthic parasites, and in treating and preventing infections with the human immunodeficiency virus.

2 Claims, 6 Drawing Sheets

Protection of Spinal Motor Neurons $p<0.001$

U.S. PATENT DOCUMENTS

| | | |
|---|---|---|
| 5,801,187 A | 9/1998 | Li et al. |
| 5,801,197 A | 9/1998 | Steiner et al. |
| 5,843,960 A | 12/1998 | Steiner et al. |
| 5,846,979 A | 12/1998 | Hamilton et al. |
| 5,846,981 A | 12/1998 | Steiner et al. |
| 5,859,031 A | 1/1999 | Hamilton et al. |
| 5,874,449 A | 2/1999 | Hamilton et al. |
| 5,898,029 A | 4/1999 | Lyons et al. |
| 6,080,753 A | 6/2000 | Lyons et al. |

OTHER PUBLICATIONS

Basi, Guriqbal S., et al., "Primary Structure and Transcriptional Regulation of GAP–43, a Protein Associated with Nerve Growth," *Cell*, vol. 49, 785–791, Jun. 19, 1987.

Beck, Klaus D., et al., "Mesencephalic Dopaminergic Neurons Protected by GDNF from Axotomy–Induced Degeneration in the Adult Brain," *Nature*, 373 (1995) 339–41.

Benowitz, Larry I., et al., "A Membrane Phosphoprotein Associated with Neural Development, Axonal Regeneration, Phospholipid Metabolism, and Synaptic Plasticity," *TINS*, vol. 10, No. 12, 1987.

Bierer, Barbara E., "Two Distinct Signal Transmission Pathways in T Lymphocytes are Inhibited by Complexes Formed Between an Immunophilin and Either FK506 or Rapamycin," *Proc. Natl. Acad. Sci. USA*, vol. 87, pp. 9231–9235, Dec. 1990.

Bisby, M.A., "Dependence of GAP43 (B50, F1) Transport on Axonal Regeneration in Rat Dorsal Root Ganglion Neurons," *Brain Research*, 458 (1988) 157–161.

Bixby, John L., "Protein Kinase C Is Involved in Laminin Stimulation of Neurite Outgrowth," *Neuron* 3(3):287–97 (1989).

Bredt, David S., Nitric Oxide Snthase Regulatory Sites, *J. Biol. Chem.* 267(16) 10976–81 (1992).

Calvo, Victor, et al., "Interleukin 2 Stimulation of p70 S6 Kinase Activity is Inhibited by the Immunosuppressant Rapamycin,"*Proc. Natl. Acad. Sci. USA*, vol. 89, pp. 7571–7575, Aug. 1992.

Chong, M.S., et al., "GAP–43 mRNA in Rat Spinal Cord and Dorsal Root Ganglia Neurons: Development Changes and Re–expression Following Peripheral Nerve Injury," *European Journal of Neuroscience*, vol. 4, pp. 83–895, 1992.

Chung, Jongkyeong, et al., "Rapamycin–FKBP Specifically Blocks Growth–Dependent Activation of and Signaling by the 70 kd S6 Protein Kinases," *Cell*, vol. 69, 1227–1236, Jun. 26, 1992.

Constantini, Lauren C., et al., "A Novel Immunophilin Ligand: Distinct Branching Effects on Dopaminergic Neurons in Culture and Neurotrophic Actions after Oral Administration in an Animal Model of Parkinson's Disease," *Neurobiology of Disease*, 5 (1998) 97–106.

Constantini, Lauren C., et al., "Immunophilin ligands can prevent progressive dopaminergic degeneration in animal models of Parkinson's disease," *European Journal of Neuroscience*, 13 (2001) 1085–92.

Dawson, Ted M., et al., "Immunosuppressant FK506 Enhances Phosphorylationof Nitric Oxide Synthase and Protects Against Glutamate Neurotoxicity," *Proc. Natl. Acad. Sci. USA*, vol. 90, pp. 9808–9812, Nov. 1993.

Dawson, Valina L., et al., "Mechanisms of Nitric Oxide—Mediated Neurotoxicity in Primary Brain Cultures," *The Journal of Neuroscience*, Jun. 1993, 13(6): 2651–2661.

Dawson, Valina L., et al., "Nitric Oxide Mediates Glutamate Neurotoxicity in Primary Cortical Cultures," *Proc. Natl. Acad. Sci. USA*, vol. 88, pp. 6368–6371, Jul. 1991.

DeFranco, Anthony L., "Immunosuppressants at Work," *Nature*, vol. 352, 754–55, Aug. 29, 1991.

Dumont, Francis J. et al., "The Immunosuppressive and Toxic Effects of FK–506 are Mechanistically Related: Pharmacology of a Novel Antagonist of FK–506 and Rapamycin," *J. Exp. Med.*, 1992, 176, 751–760.

Dumont, Francis, J., et al., "Distinct Mechanisms of Suppression of Murine T Cell Activation by the Related Macrolides FK–506 and Rapamycin," *The Journal of Immunology*, vol. 144, 251–258, No. 1, Jan. 1, 1990.

Dumont, Francis J., et al., "The Immunosuppressive Macrolides FK–506 and Rapamycin Act as Reciprocal Antagonists in Murine T Cells," *The Journal of Immunology*, vol. 144, 1418–1424, No. 4, Feb. 15, 1990.

Ferrari, Stefano, et al., The Immunosuppressant Rapamycin Induces Inactivation of $p70^{s6k}$ through Dephosphorylation of a Novel Set of Sites, *The Journal of Biological Chemistry*, vol. 268, No. 22, pp. 16091–16094, Aug. 5, 1993.

Fruman, David A., et al., "Calcineurin phosphatase activity in T lymphocytes is inhibited by FK 506 and cyclosporin A," *Proc. Natl. Acad. Sci. USA* 89 (1992) 3686–3690.

Fujita, Ko, et al., "Regulation of the Differentiation of PC12 Pheochromocytoma Cells," *Environmental Health Perspectives*, vol. 80, pp. 127–142, 1989.

Galat, Andrzej, et al., "A Rapamycin–Selective 25–kDa Immunophilin," *Biochemistry*, vol. 31, No. 8, 1992.

Gash, Don M., et al., "Functional recovery in parkinsonian monkeys treated with GDNF," *Nature*, 380 (1996) 252–255.

Girard, Peggy R., et al., "Protein Kinase C and Its 80–Kilodalton Substrate Protein in Neuroblastoma Cell Neurite Outgrowth," *Journal of Neurochemistry*, vol. 54, No. 1, 300–306, 1990.

Gold, Bruce G., et al., "The Immunosuppressant FK506 Increases Functional Recovery and Nerve Regeneration Following Peripheral Nerve Injury," *Restorative Neurology and Neuroscience*, 6 (1994) 287–296.

Grafstein, Bernice, et al., "Intracellular Transport in Neurons," *Physiological Reviews*, vol. 60, No. 4, 1167–1283, Oct. 1980.

Greene, Lloyd A., et al., "Establishment of a Noradrenergic Clonal Line of Rat Adrenal Pheochromocytoma Cells Which Respond to Nerve Growth Factor," *Proc. Natl. Acad. Sci. USA*, vol. 73, No. 7, pp. 2424–2428, Jul. 1976.

Handschumacher, Robert E., et al., "Cyclophilin: A Specific Cytosolic Binding Protein for Cyclosporin A," *Science*, vol. 226:544–546, Nov. 1984.

Hashimoto, Seiichi, et al., "Blockage of Nerve Growth Factor Action in PC12h Cells by Staurosporine, a Potent Protein Kinase Inhibitor," *Journal of Neurochemistry*, vol. 53, No. 6, 1675–85, 1989.

Hoffman, Paul N., "Expression of GAP–43, a Rapidly Transported Growth–Associated Protein, and Class II Beta Tubulin, a Slowly Transported Cytoskeletal Protein, Are Coordinated in Regenerating Neurons," *The Journal of Neuroscience*, Mar. 1989, 9(3) 893–897.

Hsiang, J., et al., "The Effects Of Nerve Growth Factor On The Development Of Septal Cholinergic Neurons In Reaggregate Cell Cultures," *Neuroscience*, 29 (1989) 209–223.

Hsu, Linda, "the Effect of 12-O-Tetradecanoylphorbol-13-Acetate (TPA) on Axonal Elongation and Fasciculation," *Anatomy and Embryology*, 1989, 179:511–518.

Ito, Akira, et al., "The Complete Primary Structure of Calcineurin A, A Calmodulin Binding Protein Homologous with Protein Phosphatases 1 and 2A," *Biochemical and Biophysical Research Communications*, vol. 163, No. 3, pp. 1492–1497, 1989.

Jackowski, A., "A Neural Injury Repair; Hope for the Future as Barriers to Effective CNS Regeneration Become Clearer," *British J. of Neurosurgery*, 9 (1995) 303–317.

Jayaraman, Thottala, et al., "FK506 Binding Protein Associated with the Calcium Release Channel (Ryanodine Receptor)", *The Journal of Biological Chemistry*, vol. 267, No. 14, pp. 9474–9477, May 15, 1992.

Jin, Yong Jiu, et al., "The 25–kDa FK506–binding Protein is Localized in the Nucleus and Associates with Casein Kinase II and Nucleolin," *Proc. Natl. Acad. Sci. USA*, vol. 90, pp. 7769–7773, Aug. 1993.

Jin, Yong–Jiu, et al., "Molecular Cloining of a Membrane-Associated Human FK506– and Rapamycin–binding Protein, FKBP–13," *Proc. Natl. Acad. Sci. USA*, vol. 88, pp. 6677–6681, Aug. 1991.

Jin, Yong–Jiu, et al., "Molecular Cloning of a 25–kDa High Affinity Rapamycin Binding Protein, FKBP25," *The Journal of Biological Chemistry*, vol. 267, No. 16, pp. 10942–10945, Jun. 5, 1992.

Kitamura, Yoshihisa, et al., "Suppressive Effect of FK–506, A Novel Immunosuppressant, Against MPTP–Induced Dopamine Depletion in the Striatum of Young C57BL/6 Mice," *Journal of Neuroimmunology*, 50 (1994) 221–224.

Kuno, Takayoshi, et al., "Evidence for a Second Isoform of the Catalytic Subunit of Calmodulin–Dependent Protein Phosphatase (Calcineurin A)," *Biochemical and Biophysical Research Communications*, vol. 165, No. 3, pp. 1352–1358, 1989.

Kunz, Jeannette, et al., "Target of Rapamycin in Yeast, TOR2, Is an Essential Phosphatidylinositol Kinase Homolog Required for $G_1$ Progression," *Cell*, vol. 73, 585–596, May 7, 1993.

Kuo, Calvin J., "Rapamycin Selectively Inhibits Interleukin–2 Activation of p70 S6 Kinase," *Nature*, vol. 358, 70–73, Jul. 2, 1992.

Levi, A., et al., "The Mode of Action of Nerve Growth Factor in PC12 Cells," *Molecular Neurobiology*, vol. 2, 201–26, 1988.

Li, Linxi, et al., "Neurotrophic Agents Prevent Motoneuron Death Following Sciatic Nerve Section in the Neonatal Mouse," *Journal of Neurobiology*, 25, 7 (1994) 759–66.

Lieberman, A.R., "The Axon Reaction: A Review of the Principal Features of Perikaryal Responses to Axon Injury," *Int. Rev. Neurobiol.* 14:49–124 (1971).

Lin, Leu–Fen H., et al., "GDNF: A Glial Cell Line—Derived Neurotrophic Factor for Midbrain Dopaminergic Neurons," *Science*, 260 (1993) 1130–32.

Liu, J., et al., "Inhibition of T Cell Signaling by Immunophilin–Ligand Complexes Correlates with Loss of Calcineurin Phosphatase Activity," *Biochemistry* 1992, 31, 3896–3901.

Liu, Jun, et al., "Calcineurin is a Common Target of Cyclophilin–Cyclosporin A and FKBP–FK506 Complexes," *Cell*, 66(4); 807–815 (1991).

Liu, Yuehueng, et al., "Dephosphorylation of Neuromodulin by Calcineurin," *J. Biol. Chem.* 264(22) 12800–04 (1989).

Lyons, W. Ernest, et al., "Immunosuppressant FK506 Promotes Neurite Outgrowth in Cultures of PC12 Cells and Sensory Ganglia," *Proc. Natl. Acad. Sci. USA*, vol. 91, pp. 3191–3195, Apr. 1994.

Magal, Ella, et al., "Effects of ciliary neuronotrophic factor on rat spinal cord neurons in vitro: survival and expression of choline acetyltransferase and low–affinity nerve growth factor receptors," *Developmental Brain Research*, 63 (1991) 141–150.

Maki, Noboru, et al., "Complementary DNA Encloding the Human T–Cell FK506–binding Protein, A Peptidylprolyl cis–trans Isomerase Distinct from Cyclophilin," *Proc. Natl. Acad. Sci. USA*, vol. 87, pp. 5440–5443, Jul. 1990.

Matsuoka, Ichiro, et al., "Cell–Type–specific Regulation of Nerve Growth Factor (NGF) Synthesis in Non–Neuronal Cells: Comparison of Schwann Cells with Other Cell Types," *The Journal of Neuroscience*, Oct. 1991, 11(10):3165–3177.

Mattson, M. P., et al., "Intracellular Messengers in the Generation and Degeneration of Hippocampal Neuroarchitecture," *Journal of Neuroscience Research*, 21:447–464 (1988).

McKeon, Frank, "When Worlds Collide: Immunosuppressants Meet Protein Phosphatases," *Cell*, vol. 66, 823–826, Sep. 6, 1991.

Mehta, Sujata, et al., "Neurite Outgrowth and Protein Phosphorylation in Chick Embryonic Sensory Ganglia Induced by a Brief Exposure to 12–O–Tetradecanoylphorbol 13–Acetate," *Journal of Neurochemistry*, vol. 60, No. 3, 972–81, 1993.

Meiri, Karina F., et al., "Monoclonal Antibodies Show That Kinase C. Phosphorylation of GAP–43 during Axonogenesis Is Both Spatially and Temporally Restricted In Vivo," *The Journal of Cell Biology*, vol. 112, No. 5, 991–1005, Mar. 1991.

Morrison, Richard S., et al., "Inhibition of Protein Kinase C Activity Promotes the Neurotrophic Actionof Epidermal and Basic Fibroblast Growth Factors," *Brain Research*, 473 (1988) 141–146.

Phelps, C.H., et al., "Commentary: Potential Use of Nerve Growth Factor to Treat Alzheimer's Disease," *Neurobiology of Aging*, vol. 10, pp. 205–207, 1989.

PR Newswire, Guilford Pharmaceuticals, Inc., "Guilford Pharmaceuticals Announces Completion of NIL–A Phase II Clinical Trial for Parkinson's Disease, First Clinical Evaluation of Neuroimmunophilin Ligands in Parkinson's Disease," Baltimore, Jul. 26, 2001.

Price, D.J., et al., "Rapamycin–Induced Inhibition of the 70–Kilodalton S6 Protein Kinase," *Science*, vol. 257:973–977, Aug. 1992.

Reinhold, David, et al., "The Lack of a Role for Protein Kinase C in Neurite Extension and in the Induction of Ornithine Decarboxylase by Nerve Growth Factor in PC12 Cells," *J. Biol. Chem.* 264(6): 3538–44 (1989).

Rosenthal, A., et al., "Primary Structure and mRNA Localizationof Protein F1, A Growth–Related Protein Kinase C Substrate Associated with Synaptic Plasticity," *The EMBO Journal*, vol. 6, No. 12, pp. 3641–3646, 1987.

Ryba, M., et al., "Cyclosporine A Prevents Neurological Deterioration of Patients with SAH—A Preliminary Report," *Acta Neurochir.* (Wien) (1991) 112:25–27.

Saika, Takanori, et al., "Effects of Nerve Crush and Transection on mRNA Levels for Nerve Growth Factor Receptor in the Rat Facial Motoneurons," *Molecular Brain Research*, 9 (1991) 157–160.

Schreiber, Stuart L., "Chemistry and Biology of the Immunophilins and Their Immunosuppressive Ligands," *Science*, vol. 251, 283–287, Jan. 18, 1991.

Schreiber, Stuart L., et al., "The Mechanisms of Action of Cyclosporin A and FK506," *Immunology Today*, vol. 13, No. 4, 1992.

Schreyer, David J., et al., "Fate of GAP–43 in Ascending Spinal Axons of DRG Neurons After Peripheral Nerve Injury: Delayed Accumulation and Correlation with Regenerative Potential," *The Journal of Neuroscience*, Dec. 1991, 11(2), 3738–3751.

Sharkey, John, et al., "Immunophillins Mediate the Neuroprotective Effects of FK506 in Focal Cerebral Ischaemia," *Nature*, vol. 371, 336–39, Sep. 22, 1994.

Shiga, Yusei, et al., "Cyclosporin A Protects Against Ischemia–Reperfusion Injury in the Brain," *Brain Research*, 595 (1992) 145–148.

Shrine, "NGF Receptors Can be Anges of Death," *Bioworld Today*, 5:1–2.

Simon, Ralph, et al., "Human CNTF and related cytokines: effects on DRG neurone survival," *Neuroreport*, 7, (1995) 153–157.

Skene, J.H. Pate, "Axonal Growth–Associated Protein," *Ann. Rep. Neurosci.* 1989, 12:127–56.

Skene, J.H. Pate, et al., "Axonally Transported Proteins Associated with Axon Growth in Rabbit Central and Peripheral Nervous Systems," *The Journal of Cell Biology*, vol. 89, Apr. 1981, 96–103.

Skene, J.H. Pate, et al., "Changes in Axonally Transported Proteins During Axon Regeneration in Toad Retinal Ganglion Cells," *The Journal of Cell Biology*, vol. 89, Apr. 1981, 86–95.

Snipes, G.J., et al., "Regulation of Specific Neuronal and Non–neuronal Proteins During Development and Following Injury in the Rat Central Nervous Sytem," *Progress in Brain Research*, vol. 71, 155–75, F.J. Seil, E. Herbert and B.M. Carlson (Eds.).

Snyder et al., "Immunophilins and the nervous system," *Nature Medicine*, vol. 1 No. 1, 32–37, Jan. 1995.

Sommervaille, T., et al., "Time–Dependent Differences in the Increase in GAP–43 Expression in Dorsal Root Ganglion Cells After Peripheral Axotomy," *Neuroscience*, vol. 45, No. 1, pp. 213–220, 1991.

Standaert, Robert F., et al., "Molecular Cloning and Overexpression of the Human FK–506–binding Protein FKBP," *Nature*, vol. 346, 671–674, Aug. 16, 1990.

Steiner, Joseph P., et al., "High Brain Densities of the Immunophilin FKBP colocalized with calcineurin," *Nature*, 584–587, vol. 358, Aug. 13, 1992.

Steiner, Joseph P., et al., "Neurotrophic Actions of Nonimmunosuppressive Analogues of Immunosuppressive Drugs FK506, Rapamycin and Cyclosporin A," *Nature Medicine*, vol. 3, No. 4, 421–28, Apr. 1997.

Steiner, Joseph P., et al., "Neurotrophic Immunophilin Ligands Stimulate Structural and Functional Recovery in Neurodegenerative Animal Models," *Proc. Natl. Acad. Sci. USA*, vol. 94, pp. 2019–2024, Mar. 1997.

Streit, Wolfgang J., et al., "Response of Endogenous Glial Cells to Motor Neuron Degeneration Induced by Toxic Ricin," *The Journal of Comparative Neurology*, 268:248–263 (1988).

Swanson, Selene K.H., et al., "Cyclosporin–mediated inhibition of bovine calcineurin by cyclophilins A and B," *Biochemistry*, vol. 89, pp. 3741–3745, May 1992.

Tai, Ping–Kaung Ku, et al., "Association of a 59–Kilodalton Immunophilin with the Glucocorticoid Receptor Complex," *Science*, vol. 256, 1315–18, May 29, 1992.

Tanaka, T. et al., "Human Leukocyte Cathepsin G. Subsite Mapping with 4–Nitroanilides, Chemical Modification, and Effect of Possible Cofactors," *Biochem.*, 1985, 24, 2040–2047.

Teichner, Angela, et al., "Treatment with Cyclosporine A Promotes Axonal Regeneration in Rats Submitted to Transverse Section of the Spinal Cord," *Journal fur Hirnforschung*, 34 (1993)3, 343–349.

Tetzlaff, W., et al., "Axonal Transport and Localization of B–50/GAP–43–like Immunoreacitivty in Regenerating Sciatic and Facial Nerves of the Rat," *The Journal of Neuroscience*, Apr. 1989, 9(4), 1303–1313.

Tetzlaff, Wolfram, et al., "Response of Facial and Rubrospinal Neurons to Axotomy: Changesin mRNA Expression for Cytoskeletal Proteins and GAP–43," *The Journal of Neuroscience*, Aug. 1991, 11(8): 2528–2544.

Thoenen, H., et al., "Physiology of Nerve Growth Factor," *Physiological Reviews*, vol. 60, No. 4, 1284–1335, Oct. 1980.

Timerman, Anthony P., et al., "The Calcium Release Channel of Sarcoplasmic Reticulum is Modulated by FK–506–binding Protein," *The Journal of Bilogical Chemistry*, 268 (31): 22992–9 (1993).

Tindall, Richard S.A., "Immunointervention with Cyclosporin A in Autoimmune Neurological Disorders," *Journal Autoimmun.* 1992 Apr., 5 Suppl. A: 301–13.

Tomac, A., et al., "Protection and repair of the nigrostriatal dopaminergic system by GDNF in vivo," *Nature*, 373 (1995) 335–9.

Trupp, Miles, et al., "Peripheral Expression of Biological Activities of GDNF, a New Neurotrophic Factor for Avian and Mammalian Peripheral Neurons," *Journal of Cell Biology*, 130 (1995) 137–148.

Tuszynski, Mark H., et al., "Nerve Growth Factor Infusion in the Primate Brain Reduces Lesion–Induced Cholinergic Neuronal Degeneration," *Journal of Neuroscience*, 10, 11(1990) 3604–3614.

Van der Zee, Catharina E.E.M., et al., "Expression of Growth–Associated Protein B–50 (GAP43) in Dorsal Root Ganglia and Sciatic Nerve During Regenerative Sprouting," *The Journal of Neuroscience*, Oct. 1989, 9(10), 3505–3512.

Verge, V.M.K., et al., "Correlation Between GAP43 and Nerve Growth Factor Receptors in Rat Sensory Neurons," *The Journal of Neuroscience*, Mar. 1990, 10(3), 926–934.

Wiese, U.H., et al., "Differential Expression of Growth–Associated Protein (GAP–43) mRNA in Rat Primary Sensory Neurons After Peripheral Nerve Lesion: A Non–Radioactive In Situ Hybridisation Study," *Brain Res.* 592:141–56 (1992).

Wiley, Ronald G., et al., "Suicide Transport: Destruction of Neurons by Retrograde Transport of Ricin, Abrin, and Modeccin," *Science*, vol. 216:889–890, May 1982.

Williams, Lawrence R., et al., "Continuous infusion of nerve growth factor prevents basal forebrain neuronal death after fimbria fornix transection," *Proc. Natl. Acad. Sci.*, 83, (1986) 9231–9235.

Woolf, C.J., et al., "The Growth–Associated Protein GAP–43 Appears in Dorsal Root Ganglion Cells and in the Dorsal Horn of the Rat Spinal Cord Following Peripheral Nerve Injury," *Neuroscience* 34(2): 465–78 (1990).

Yankner, Bruce A., et al., "Transfection of PC12 Cells with the Human GAP–43 Gene: Effects on Neurite Outgrowth and Regeneration," *Molecular Brain Research*, 7 (1990) 39–44.

Yem, Anthony W., et al., "The Hsp56 Component of Steroid Receptor Complexes Binds to Immobilized FK506 and Shows Homology to FKBP–12 and FKBP–13," *The Journal of Biological Chemistry*, vol. 267, No. 5, pp. 2868–2871, Feb. 15, 1992.

* cited by examiner-

NON-PEPTIDIC CYCLOPHILIN BINDING COMPOUNDS AND THEIR USE

This invention relates to pharmaceutical compositions and methods of using non-peptidic cyclophilin-binding compounds in medical conditions involving breakdown of mitochondrial energy metabolism induced by calcium overload, in treating alopecia and promoting hair growth, in treating infections with filarial and helmintic parasites, and in treating and preventing infections with the human immunodeficiency virus.

The cyclic undecapeptide cyclosporin A (CyA), as well as two other drugs, FK-506 and rapamycin, are well-known in the art as potent T-cell specific immunosuppressants, and are effective against graft rejection after organ transplantation. In vivo and in vitro, these compounds bind to two distinct classes of proteins commonly known as immunophilins. Cyclophilins (CyP), which bind cyclosporin A, and FK506-binding proteins (FKBP), which bind FK-506 and rapamycin, are both subclasses of this group of proteins termed immunophilins. Immunophilins were first identified as proteins that bind to the immunosuppressive drugs cyclosporin A, FK506, and rapamycin. CyPs and FKBPs can also be separated based on their differing structures.

The effects of the cyclosporin A:cyclophilin interaction have been well documented. Cyclosporin A binds with a dissociation constant in the range of $10^{-8}$ mol/L, a value representing a relatively high degree of attraction (Handschumacher et al., *Science* 226:544 (1984)). While the present invention is not bound by any particular theory, it appears the complex formed between CyP and cyclosporin A exerts the effects on the organism and cells, which leads to immunosuppression. The complex interacts with the cellular enzyme calcineurin, a calmodulin-dependent phosphatase, and the interaction prevents T cell activation by blocking RNA transcription of the T cell growth factor interleukin 2 (IL-2). (Palacios, *J. Immunol.* 128:337 (1982)). Without IL-2 to cause T cell proliferation, specific T cell populations cannot mount a strong immune response, resulting in immunosuppression.

A number of types of mammalian cyclophilins have been identified and cloned, cyclophilins A, B, C, D, and cyclophilin-40 (Snyder and Sabatini, *Nat. Med.* 1:32–37 (1995); Friedman et al., *Proc. Natl. Acad. Sci.*, 90:6815–6819 (1993)). Cyclophilin A is a 19 kD protein, which is abundantly expressed in a wide variety of cells. Like the other cyclophilins, cyclophilin A binds the immunosuppressive agent cyclosporin A and possesses peptidyl-prolyl cis-trans isomerase (PPIase) and protein folding or "chaperone" activities. PPIase activity catalyzes the conversion of proline residues in a protein from the cis to the trans conformation (Fischer, et al., *Biomed. Biochem. Acta* 43:1101–1112 (1984)). Cyclophilin B possesses an N-terminal signal sequence that directs translocation into the endoplasmic reticulum of the cell. The 23 kD cyclophilin C is found in the cytosol of the cell. Cyclophilin D, at 18 kD, appears to target its actions in the mitochondria. And cyclophilin-40 is a component of the inactivated form of a glucocorticoid receptor.

Since immunophilins, including the cyclophilin group of proteins, were discovered because of their interaction with known immunosuppressive drugs, drug discovery efforts initially focused on improving the immunosuppressant potency, and optimizing the pharmacological profile, of cyclosporin A and its peptidic analogues for immunosuppressant uses. Later, other biological effects of immunosuppressant cyclophilin-binding drugs were discovered. It has been reported that, in murine models which mimic human premature hair follicle regression or human chemotherapy-induced hair loss, topical application of CsA induces and maintains hair growth, and topical or systemic administration of CsA protects from hair loss induced by cancer chemotherapeutic agents (see, e.g., Maurer, et al. *Am. J. Pathol.* 150(4): 1433–41 (1997); Paus, et al., *Am. J. Pathol.* 144, 719–34 (1994)). One form of hair loss, alopecia areata, is known to be associated with autoimmune biological processes; hence, topically administered immunomodulatory compounds are expected to be efficacious in treating this particular form of hair loss. However, there is evidence that initiation of hair growth by CsA is unrelated to immunosuppression (Iwabuchi, et al., *J. Dermatol. Sci.* 9, 64–69 (1995)).

FK506 has also been shown to stimulate hair growth in a dose-dependent manner when administered topically (Yamamoto, et al., *J. Invest. Dermatol.* 102 (1994) 160–164; Jiang, et al., *J. Invest. Dermatol.*, 104 (1995) 523–525).

The use of cyclosporin A and related compounds for hair revitalization has been disclosed in U.S. Pat. No. 5,342,625 (Hauer et al.), U.S. Pat. No. 5,284,826 (Eberle), U.S. Pat. No. 4,996,193 (Hewitt et al.). These patents relate to compounds and compositions useful for treating immune-related disorders and cite the known use of cyclosporin and related immunosuppressive compounds for hair growth. The known utility of cyclosporin A in promoting hair growth has also been cited in earlier work by the present inventors, see, e.g., U.S. Pat. No. 6,172,087 B1 (Steiner and Hamilton), U.S. Pat. No. 6,177,455 B1 (Steiner and Hamilton), U.S. Pat. No. 6,187,784 B1 (Steiner and Hamilton).

Another biological activity of the cyclophilin-binding compounds cyclosporin and its peptidic analogues relates to their protective effects on proapoptotic cells. The mitochondrion is increasingly being recognized as an important mediator of cell death in hypoxia, ischemia, and chemical toxicity. Disruption of the mitochondrial transmembrane potential is observed before other features of apoptosis (e.g. generation of reactive oxygen species or internucleosomal DNA fragmentation ("laddering")) become detectable. This applies to many different models of apoptosis induction, such as, for example, NGF-deprivation of cultured sympathetic neurons, dexamethasone-induced lymphocyte apoptosis, programmed lymphocyte death, activation-induced programmed cell death of T cell hybridomas, and tumor necrosis factor-induced death of lymphoma cells. [Marchetti, P., et al., J. Exp. Med. 184, 1996, 1155–1160]. Breakdown of mitochondrial transmembrane potential in proapoptotic cells has been attributed to the formation of an unspecific high conductance channel—the mitochondrial permeability transition pore—which leads to an increased permeability of the inner mitochondrial membrane to small molecular weight solutes. The ensuing release of intramitochondrial ions, influx of solutes, uncoupling of oxidative phosphorylation, and loss of metabolic intermediates accompanies large amplitude mitochondrial swelling and a depletion of cellular energy stores [see, e.g., Lemasters, J. J. et al., Mol. Cell. Biochem. 174 (1997) 159–165]. Importantly, CsA and non-immunosuppressive peptidic CsA analogues have been described to potently block pore conductance and inhibit the onset of the mitochondrial permeability transition [Broekemeier, K. M., et al., J. Biol. Chem. 264 (1989) 7826–7830; Zamzami, M., et al., FEBS Lett. 384 (1996) 53–7]. The mitochondrial permeability transition pore forms under calcium overload conditions such as occur in ischemia/reperfusion injury, and it has been found that administration of CsA and/or non-immunosuppressive peptidic CsA analogues, by blocking the permeability transition pore, leads to significant protection in experimental models of cerebral stroke [Matsumoto, S., et al., J. Cereb. Blood Flow Metab. 19 (1999) 736–41], cardiac ischemia [Griffiths, E. J. and Halestrap, A. P., J. Mol. Cell Cardiol. 25 (1993) 1461–1469], and hepatic ischemia/reperfusion injury [Leducq, N., et al., Biochem. J. 336 (1998) 501–6 ].

CsA and its non-immunosuppressive peptidic analogues have also been found to potently inhibit the growth of pathogenic protozoan parasites, such as *Cryptosporidium parvum, Plasmodium falciparum, Plasmodium vivax, Schistosoma spec.*, and *Toxoplasma gondii* [Perkins, et al., *Antimicrob. Agents Chemother.*42: 843–848 (1998)]. Although antiprotozoan activity appears not to be correlated with immunosuppressive or PPIase inhibitory activity [Bell, et al., *Biochem. Pharmacol.* 48:495–503 (1994); Khattab, et al., *Exp. Parasitol.* 90:103–109 (1998)], the protozoan cyclophilin, complexed to CsA or its non-immunosuppressive peptidic analogues, has been proposed to play an active role in mediating the antiparasitic effects of cyclophilin ligands [Berriman and Fairlamb, *Biochem. J.* 334:437–445 (1998)].

CyA and its non-immunosuppressive analogues also inhibit reproduction of filarial parasites in vivo with a potency unrelated to their immunosuppressive activity and their activity against Plasmodium [Zahner and Schultheiss, *J. Helminthol.* 61:282–90 (1987)], and have been shown to exert direct antihelmintic effects [McLauchlan, et al., *Parasitology* 121:661–70 (2000)].

CsA has also been found to be useful in affecting the viral replication process of the HIV-1 virus. The infectivity of the HIV-1 virus is believed to depend critically upon an interaction of the viral Gag polyprotein capsid complex with host Cyclophilin A. [Streblow et al. Virology 1998: 245, 197–202; Li et al. J. Med. Chem. 2000: 43,1770–9 ].

The aforementioned biological activities, which are believed to depend on the binding of a cyclophilin ligand to the native cyclophilin protein, may be of great therapeutic value in treating a range of medical conditions in animals, including humans. However, it is not desirable to treat conditions related to hair loss, mitochondrial energy breakdown, or HIV- or parasitic infections with an immunosuppressant cyclophilin ligand such as cyclosporin A. Furthermore, cyclophilin ligands known in the art to date are large molecules based on the peptidic structure of CsA. There thus exists an unmet need for non-immunosuppressive small molecule ligands of cyclophilin-type immunophilin proteins which are useful in the prevention or therapy of disease conditions relating to hair loss, breakdown of mitochondrial energy metabolism, HIV-infection, and infection with protozoan and helmintic parasites.

The present invention provides methods of preventing or retarding hair loss in patients undergoing therapy with doxorubicin, carboplatin, cisplatin, cyclophosphamide, dactinomycin, etoposide, hexamethamelamine, ifosfamide, taxol, vincristine, bleomycin, 5-fluorouracil, and other agents useful in the therapy of cancer, comprising administering to said patients an effective amount of a compound of formula I or II:

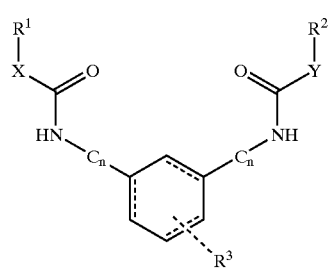

Formula I where n in $C_n$ is 0 or 1;
the dashed bond symbol represents an optional bond;
X and Y may independently be N, NH, O, S, or a direct bond;
$R^1$ is the same or different from $R^2$, and either can be
one or more C1–C6 branched or straight chain alkyl or alkenyl groups;
one or more C1–C3 branched or straight chain alkyl groups substituted by one or more Q groups;
or one or more Q groups,
where Q, which is optionally saturated, partially saturated, or aromatic, is a mono-, bi-, or tricyclic, carbo- or heterocyclic ring, wherein each ring may be optionally substituted in one to five positions with halo, hydroxyl, nitro, trifluoromethyl, acetyl, aminocarbonyl, methylsulfonyl, oxo, cyano, carboxy, C1–C6 straight or branched chain alkyl or alkenyl, C1–C4 alkoxy, C1–C4 alkenyloxy, phenoxy, benzyloxy, amino, or a combination thereof, and wherein the individual ring sizes are 5–6 members, and wherein each heterocyclic ring contains 1–6 heteroatoms selected from the group consisting of O, N, S, or a combination thereof;
and $R^3$ many be one to three substituents chosen from the group consisting of halo, hydroxyl, nitro, trifluoromethyl, C1–C6 straight or branched chain alkyl or alkenyl, C1–C4 alkoxy, C1–C4 alkenyloxy, phenoxy, benzyloxy, amino, Q as defined above, or a combination thereof;

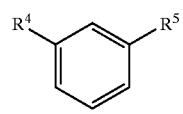

Formula II where $R^4$ and $R^5$ may independently be
—N—SO$_2$—R,
—SO$_2$—NRR,
—O—R,
—CO—N—R,
—N—CO—R,
—CO—R,
wherein each R may independently be hydrogen, Q, or a C1–C6 branched or straight alkyl or alkenyl chain, which may be substituted in one or more positions by C3–C8 cycloalkyl or cycloalkenyl, hydroxyl, or carbonyl oxygen, and where in said alkyl or alkenyl chain one or more carbon atoms are either optionally substituted with Q, or optionally replaced by O, S, SO, SO$_2$, N, or NH; where Q, which is optionally saturated, partially saturated, or aromatic, is a mono-, bi-, or tricyclic, carbo- or heterocyclic ring, wherein each ring may be optionally substituted in one to five positions with halo, hydroxyl, nitro, trifluoromethyl, acetyl, aminocarbonyl, methylsulfonyl, oxo, cyano, carboxy, C1–C6 straight or branched chain alkyl or alkenyl, C1–C4 alkoxy, C1–C4 alkenyloxy, phenoxy, benzyloxy, amino, or a combination thereof, and wherein the individual ring sizes are 5–6 members, and wherein each heterocyclic ring contains 1–6 heteroatoms selected from the group consisting of O, N, S, or a combination thereof.

The present invention further provides a method of promoting hair growth in patients suffering from hair loss associated with treatment with one or a combination of the aforementioned chemotherapeutic agents, comprising administering to said patients an effective amount of a compound of Formula I or II.

The present invention further provides a method of preventing or retarding hair loss in patients undergoing radiation therapy, comprising administering to said patients an effective amount of a compound of Formula I or II.

The present invention further provides a method of promoting hair growth in patients suffering from hair loss associated with radiation therapy, comprising administering to said patients an effective amount of a compound of Formula I or II.

The present invention further provides a method of promoting hair growth in patients suffering from alopecia areata, androgenetic alopecia/male pattern baldness, anagen effluvium, trichotillomania, traction alopecia, telogen effluvium, and hair loss induced by drugs such as, for example, methotrexate, nonsteroidal anti-inflammatory drugs, or beta blockers, comprising administering to said patients an effective amount of a compound of Formula I or II.

For these purposes, the compounds may be administered as part of pharmaceutical or cosmetic compositions, singly, in combination with other compounds of the invention, in combination with other hair growth-promoting or hair-loss preventing agents, or in combination with one or several other active agents such as, for example, antibiotic agents, antidandruff agents, and anti-inflammatory agents. Thus, the invention provides pharmaceutical or cosmetic compositions especially formulated for topical application to the skin.

The invention further provides a method of blocking the mitochondrial permeability transition pore, comprising contacting the mitochondrion with a compound of Formula I or II.

The invention further provides a method of inhibiting breakdown of mitochondrial metabolism in cells which undergo oxidative stress, comprising contacting said cells with a compound of formula I or II.

The invention further provides a method of preventing or delaying cell death in a cell subjected to calcium overload, comprising contacting said cell with a compound of Formula I or II.

The invention further provides a method of preventing, mitigating, or delaying excitotoxic or hypoglycemic injury to cells, tissues or organs both in vitro and in vivo, comprising contacting said cells, tissues, or organs with a compound of Formula I or II.

The invention further provides a method of inhibiting breakdown of energy metabolism and cell death of mammalian cells following physiological induction of programmed cell death, comprising contacting said cells with a compound of Formula I or II.

The invention further provides a method of inhibiting breakdown of energy metabolism and cell death of mammalian cells following physiological stress related to hypoxia, hypoglycemia, excitotoxic insult, or calcium overload, comprising contacting said cells with a compound of Formula I or II.

The invention further provides a method of preventing or delaying the death of cells in large scale/commercial scale cell culture, comprising contacting said cells with a compound of Formula I or II.

The invention further provides a method of using a compound of Formula I or II in the diagnosis, cure, mitigation, treatment, or prevention of ischemic injury or ischemia/reperfusion injury, comprising administering to a patient at risk for, or suffering from, an ischemic or ischemia/reperfusion injury an effective amount of a compound of Formula I or II.

The invention further provides a method of using a compound of Formula I or II in the diagnosis, cure, mitigation, treatment, or prevention of ischemic injury or ischemia/reperfusion injury, comprising administering to a patient at risk for, or suffering from, an ischemic or ischemia/reperfusion injury an effective amount of a compound of Formula I or II, wherein the ischemic injury or ischemia/reperfusion injury is selected from the group consisting of mesenteric infarction, bowel ischemia, hepatic infarction, renal infarction, splenic infarction, and ischemic heart disease.

The invention further provides a method of using a compound of Formula I or II in the diagnosis, cure, mitigation, treatment, or prevention of ischemic injury or ischemia/reperfusion injury, comprising administering to a patient at risk for, or suffering from, an ischemic or ischemia/reperfusion injury an effective amount of a compound of Formula I or II, wherein the ischemic injury or ischemia/reperfusion injury is related to congestive heart failure, myocardial ischemia, or coronary heart disease.

The invention further provides a method of treating an ophthalmic disorder in an animal, comprising administering to said animal a therapeutically effective amount of a compound of Formula I or II.

The invention further provides a method of treating an ophthalmic disorder in an animal, comprising administering to said animal a therapeutically effective amount of a compound of Formula I or II, wherein said ophthalmic disorder is glaucoma, ischemic retinopathy, vascular retinopathy, or degeneration of the photoreceptor cell layer.

The invention further provides a method of treating Reye's syndrome in a patient, comprising administering to said patient a therapeutically effective amount of a compound of Formula I or II.

The invention further provides a method of preventing or reducing tissue damage of organs used in organ transplantation surgery, comprising contacting said organs with a compound of Formula I or II.

The invention further provides a method of treating an infection with pathogenic protozoan or helmintic parasites, comprising contacting said parasites with a compound of Formula I or II.

The invention further provides a method of treating an infection with pathogenic protozoan or helmintic parasites in an animal, comprising administering to said animal a therapeutically effective amount of a compound of Formula I or II.

The invention further provides a method of treating a medical condition related to infection with pathogenic protozoan or helmintic parasites in an animal, comprising administering to said animal a therapeutically effective amount of a compound of Formula I or II, wherein said medical condition is malaria, river blindness, lymphatic filariasis, intestinal roundworm infection, tapeworm infection, pinworm infection, toxoplasmosis, leishmaniasis, trypanosomiasis, or bilharzia.

The invention further provides a method for treating infection with a virus of the HIV type in a patient, comprising administering to said patient a therapeutically effective amount of a compound of Formula I or II.

The invention further provides a method for treating acquired immune deficiency syndrome (AIDS) in a patient, comprising administering to said patient a therapeutically effective amount of a compound of Formula I or II.

A number of compounds can be selected for use from Formulae I and II. For example, starting with a particular compound, any of the individual variable groups $R^1$–$R^5$, X, Y, and a value for 'n' can be selected while one or more of the other variable groups can be modified. For example, in Formula I, the "n" can be set at 0 to select subgroups of related compounds with X and Y being both NH, or both being O, or X being NH and Y being O, and within each of those 3 groups $R^3$ being present or absent, and then within each of those 6 groups the 6-membered ring structure is either a cyclohexyl or an aromatic ring, which results in 12 subgroups of related compounds. Any of those 12 subgroups can be selected and further divided into additional subgroups of compounds defined by having an $R^1$ the same as $R^2$ or by having both $R^1$ and $R^2$ comprise a substituted benzyl or substituted phenyl group. This process can be repeated using any one or combination of the variable groups. In this way, one skilled in the art can select and use groups of related compounds or even individual compounds, all within the invention. Many examples are shown below; however, they are merely representative of the scope of changes and modifications possible. One skilled in the art can devise many separate compounds from the description of the Formulae alone. Thus, the invention specifically includes numerous individual compounds that fall within the definition of either Formula I or II.

Compounds of Formulae I and II may be prepared or formulated as a salt or derivative for some uses, including pharmaceutical and tissue or cell culture uses. The compounds of the invention can also be part of a composition comprising one or more compounds of Formula I or II. Thus, pharmaceutically acceptable salts and derivatives of any of the compounds, or compositions comprising them, are specifically included in this invention. A compound of Formula I or II, or a compound having Formulae I or II, will optionally include the salt or derivative of the compound depicted in the formula.

The compounds of the invention can be produced as a mixture of isomers or racemic mixtures or as optically pure compounds. Methods for separating stereoisomers can also be used to enrich mixtures for one or more compounds. The compositions of the invention may similarly contain mixtures of stereoisomers, mixtures of one or more stereoisomers, or be enriched for one or more stereoisomers. All of these forms are specifically included in this invention.

Preferably, compounds of Formulae I and II selectively bind to a CyP as detected, for example, by a measurable inhibition of the rotamase (PPIase or peptidyl-prolyl cis-trans isomerase enzyme) activity of CyP. "Selectively bind to a CyP" means the compounds do not possess a significant binding affinity toward a FKBP and/or do not possess a biological activity associated with binding to a FKBP. For example, the $IC_{50}$ towards FKBP is at or above 10 $\mu$M or at or above 50 $\mu$M. The skilled artisan is familiar with ways to detect rotamase inhibition in CyP and FKBP. In addition, a number of ways for detecting binding to a CyP are described below.

As is readily apparent from Formulae I and II, a common 1-,3-substitution pattern on a central ring structure exists. This common pattern differs from the approaches previously taken to identify other immunophilin binding compounds or drugs. For example, Holt et al. (*Bioorg. Med. Chem. Letters,* 4: 315–320 (1994)) discuss a pipecolate, or 1-(1,2-dioxo) 2-carboxylate piperidine containing base structure for binding to FKBP. Similarly, earlier work by the inventors established the relevance of a 1-(1,2-dioxo) 2-carboxylate pyrrolidine containing structure for binding to FKBP (Steiner et al., *PNAS* 94:2019–2024 (1997)). Presumably, these structures mimic the natural substrate for the rotamase activity, a proline-containing fragment of a protein. In a protein, the amino acid proline corresponds to a 1,2-substituted pyrrolidine structure. Prior work has generally incorporated that structure. However, Formulae I and II do not correspond to a 1,2-substituted pyrrolidine structure. Yet, as demonstrated here, compounds of these formulae possess important bioactive and biochemical functions.

The body of work related to analogues of cyclosporin A, FK-506, and rapamycin further distances the compounds of this invention from prior work. (See, for example, U.S. Pat. Nos. 5,767,069, 5,284,826, 4,703,033, and 5,122,511.) These analogues typically possess a cyclic peptide structure.

In another aspect, the invention relates to methods for binding non-peptidic compounds to cyclophilin-type immunophilins. Binding results in an "immunophilin:drug" complex, which is considered to be the active agent in the in vivo immunosuppressive and neurotrophic activities of rotamase inhibitors (Hamilton and Steiner, *J. of Med. Chem.* 41:5119–5143 (1998); Gold, *Mol. Neurobiol.* 15:285–306 (1997)). Whether or not the complex acts for any or all the therapeutic actions of these rotamase inhibitors, focusing on the immunophilin:drug interaction has led to the discovery of a number of new drug compounds. Accordingly, methods of using compounds, such as those of Formulae I and II, to create an immunophilin:compound complex, or a CyP:compound complex, provides an important aspect of this invention. This aspect can be exploited, for example, in methods where the compound, or a mixture comprising one or more of the compounds of the invention, is administered to cells in culture or to an animal.

While the immunophilin:compound complex has beneficial effects in vivo and in cultured cells, numerous other uses for binding the compounds to an immunophilin exist. For example, in vitro binding experiments can be used to identify and purify cellular components that interact with the immunophilin complex. An affinity chromatography column or matrix bearing the compound can be reacted with a CyP, and cellular or tissue extracts passed over the column or matrix.

Thus, the invention also provides methods for forming immunophilin:compound or CyP:compound complexes as well as the complexes themselves. To form these complexes, the compounds can contact an immunophilin or CyP protein in vivo, in vitro, or within a cell. In preferred embodiments, the compound contacts a human CyP protein, such as one or more of CyP A, B, C, or D. The CyP protein can be native to the cell or organism, produced via recombinant DNA, produced by other manipulations involving introduced genetic material, or produced by synthetic means. Furthermore, chimeric proteins possessing immunophilin domains that function to bind immunophilin ligands can also be used to form a protein:compound complex. The formation of the CyP:compound, immunophilin:compound, or protein:compound complex need not be irreversible.

The binding of a compound to a CyP can be detected in a number of ways, including rotamase inhibition assay, affinity chromatography, in vivo cardioprotection assay, in vitro mitochondrial permeability transition assay, or by any of the activities in experimental models of hair loss, parasitic infection, stroke, ischemia and reperfusion injury as described below, in the examples, or in the cited references.

The invention also provides compositions comprising at least one compound of Formula I or II. The compositions may comprise one or more pharmaceutically acceptable carriers, excipients, or diluents. These compositions, or the compounds themselves or mixtures of them, can be administered to an animal. Administration can be one method to allow the compound to contact a CyP within the animal. As one skilled in the art would recognize, various routes of administration are possible. Exemplary routes are specifically described in the detailed description below.

The following detailed description should not be taken as a limitation on the scope of the invention. The embodiments and examples given are illustrative of the invention. Additional aspects of the invention can be devised by reference to this disclosure as a whole in combination with the references cited and listed throughout and at the end of the specification and the knowledge of one skilled in the art. All of the references cited and listed can be relied on, in their entirety, to allow one to make and use these additional aspects of the invention.

BRIEF DESCRIPTION OF THE DRAWINGS

For each of FIGS. 1–6, the bar graphs represent the number of viable neurons after a specified treatment regimen employed in a neuroprotective activity assay. The cells of the experiments were treated with a control solution, a neurotoxic solution, and neurotoxic+experimental compound solution. The statistical significance, p, is calculated using the standard 2 tailed Student's t test.

DETAILED DESCRIPTION OF EXEMPLARY EMBODIMENTS

Figure 1:
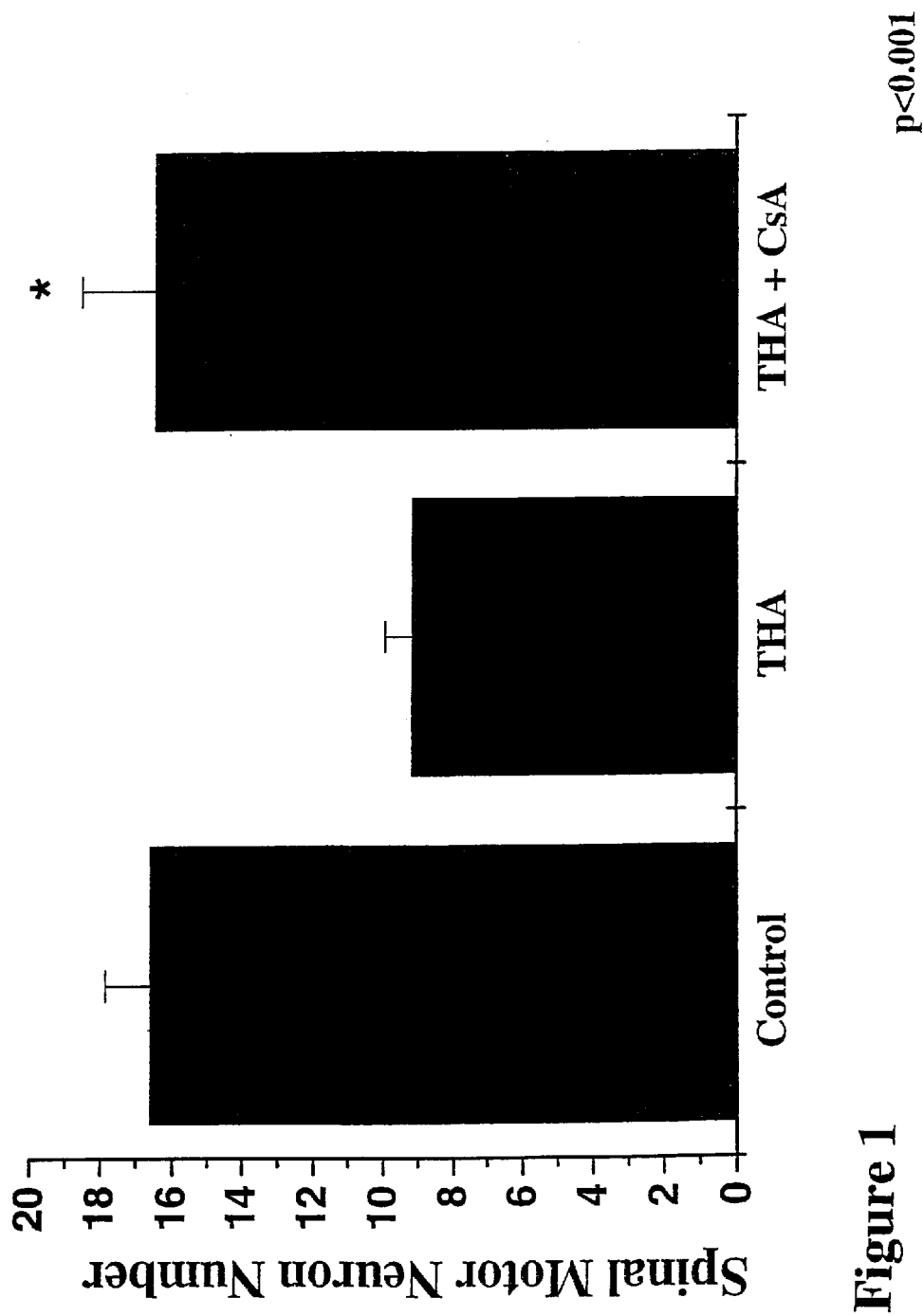
FIG. 1: Primary cultures of spinal motor neurons were treated with control (vehicle), THA neurotoxin, and THA+ cyclopsporin A (CsA), as detailed in the examples. The results show that CsA treatment maintains neuronal viability, which indicates neuroprotective activity.

One skilled in the art can refer to general reference texts for detailed descriptions of known techniques discussed herein or equivalent techniques. These texts include *Current Protocols in Molecular Biology* (Ausubel, et al., eds., John Wiley & Sons, N.Y., and supplements through June 1999), *Current Protocols in Immunology* (Coligan, et al., eds., John Wiley and Sons, N.Y., and supplements through June 1999), and *Current Protocols in Pharmacology* (Enna et al., eds., John Wiley & Sons, N.Y., and supplements through June 1999) for example, each of which are specifically incorporated by reference in their entirety. These texts can also be referred to in making or using an aspect of the invention.

As noted above, cyclosporin A was the first compound identified to bind a CyP. Based on the cyclic structure of cyclosporin A, a number of large, usually cyclic peptides were developed as immunosuppressive compounds that bind CyP. Now, unexpectedly, the inventors have found a non-peptidic class of CyP binding compounds with activity in neuronal cells.

The following compounds are representative of those useful in the methods of this invention.

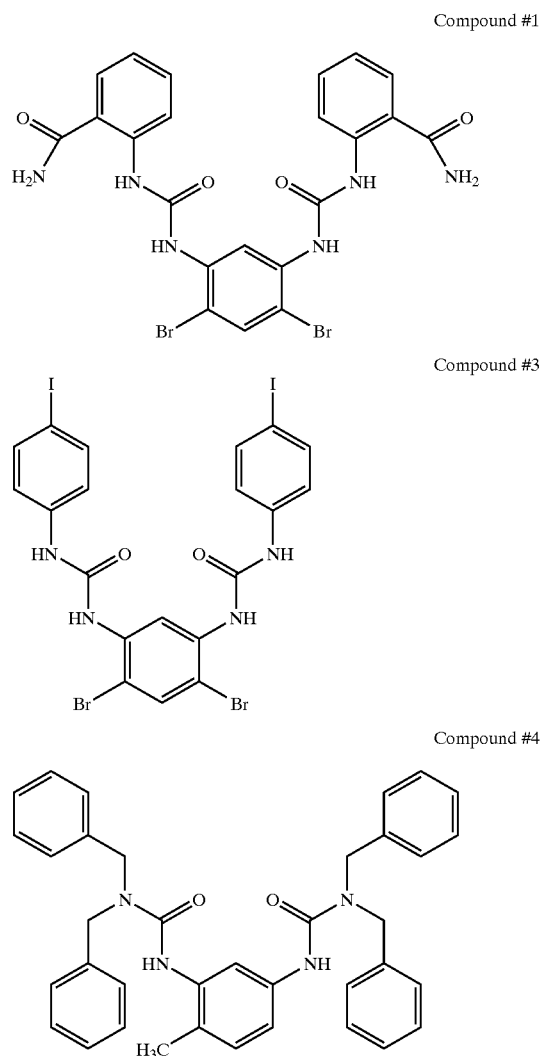

Compound #6
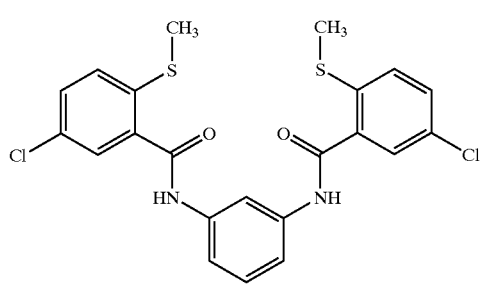
Compound #7
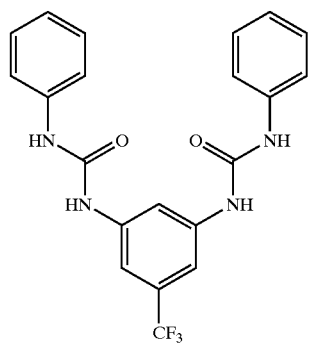
Compound #9
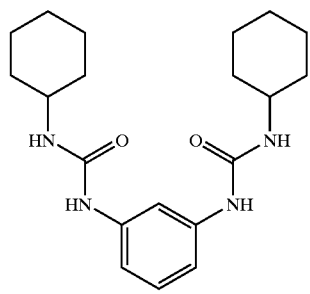
Compound #10
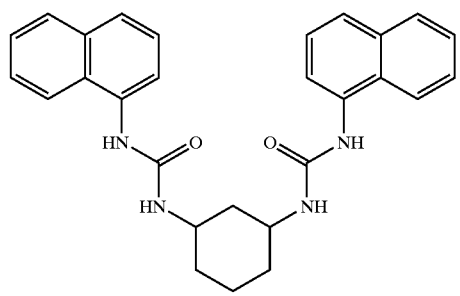
Compound #11
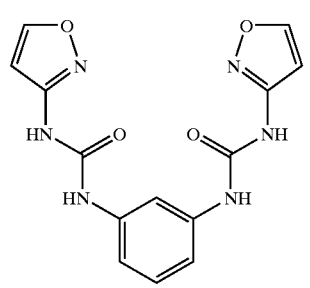
Compound #12
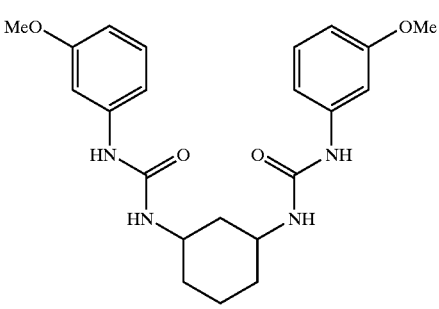
Compound #13
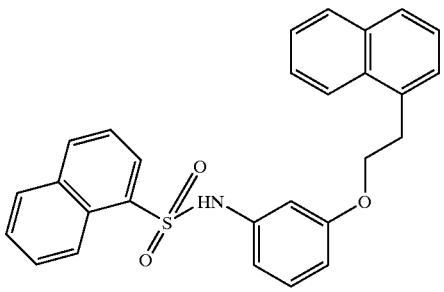
Compound #14
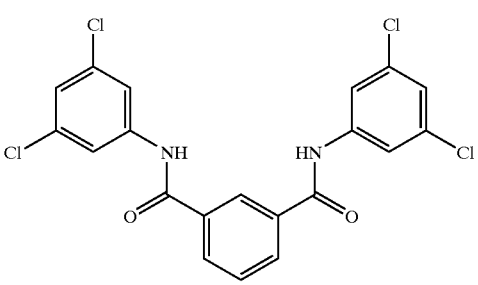
Compound #15
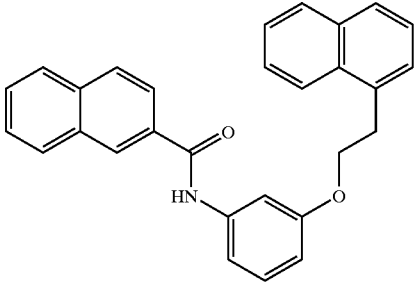
Compound #16

Compound #17
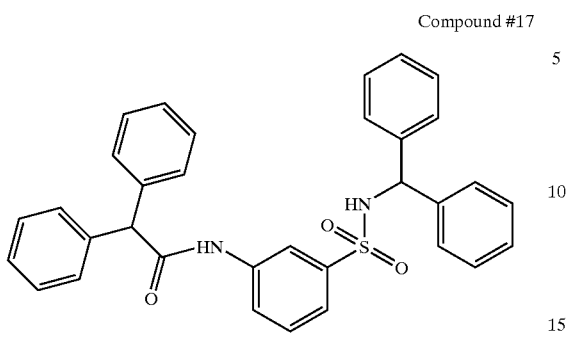
Compound #18
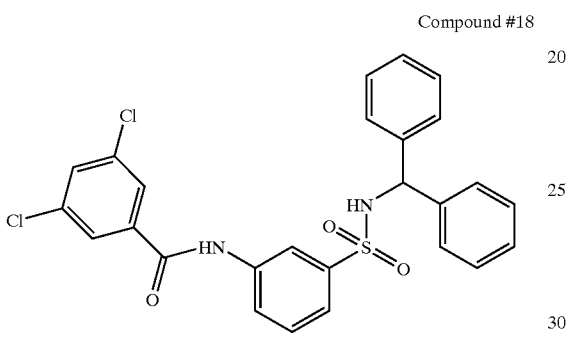
Compound #19
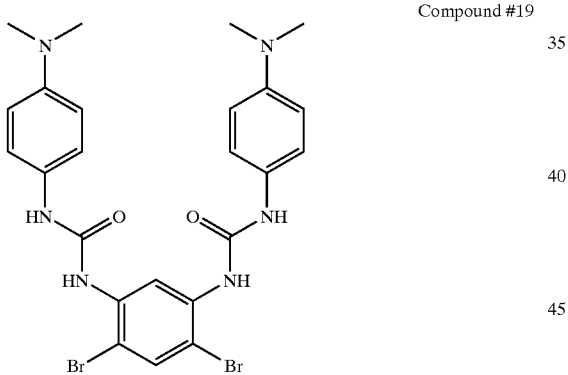
Compound #20
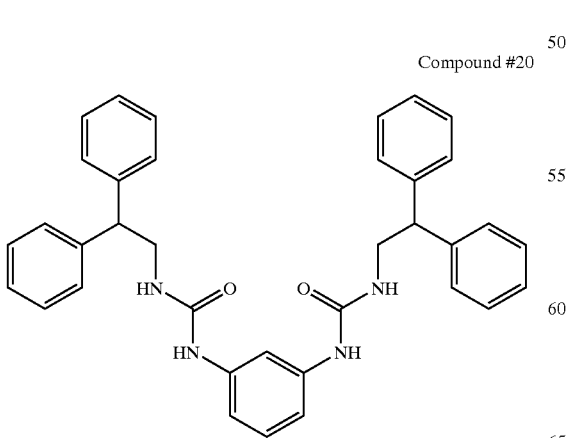
Compound #21
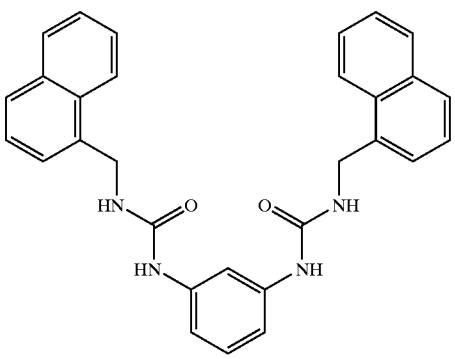
Compound #22
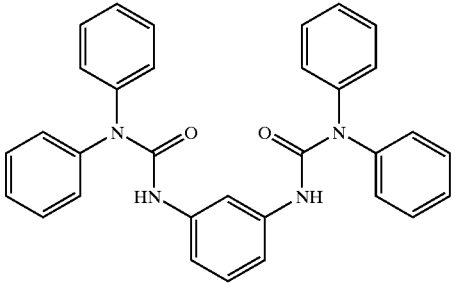
Compound #23
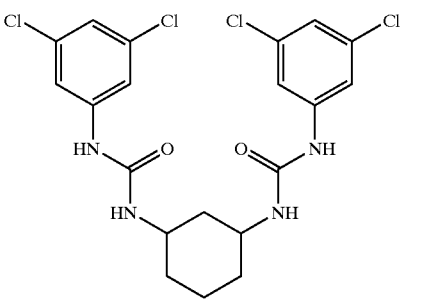
Compound #24
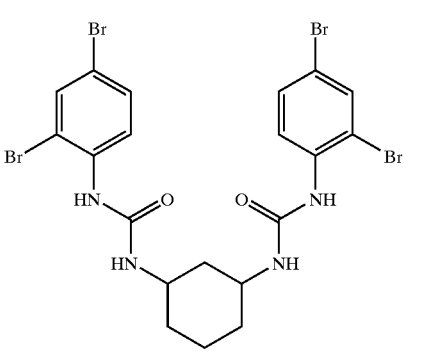
Compound #25
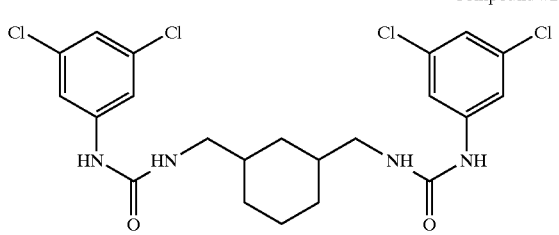

Compound #26
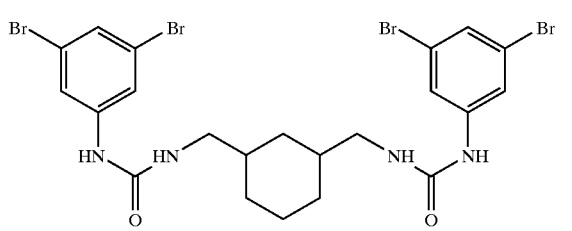

Compound #27
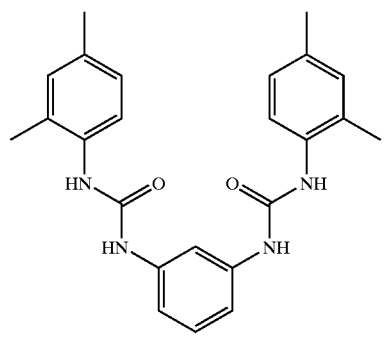

Compound #28
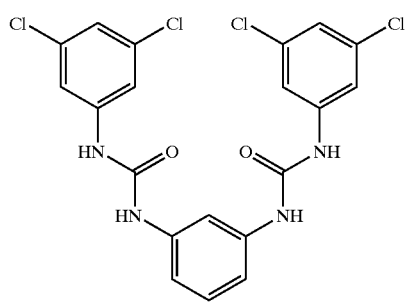

Compound #29
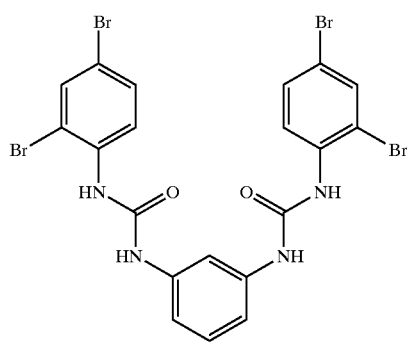

Compound #30
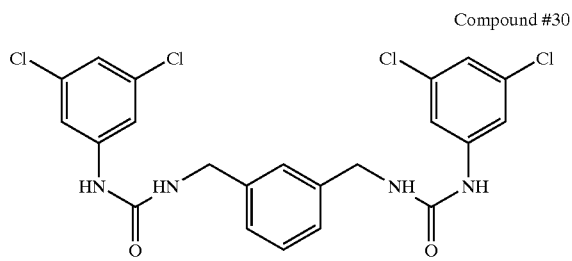

Compound #31
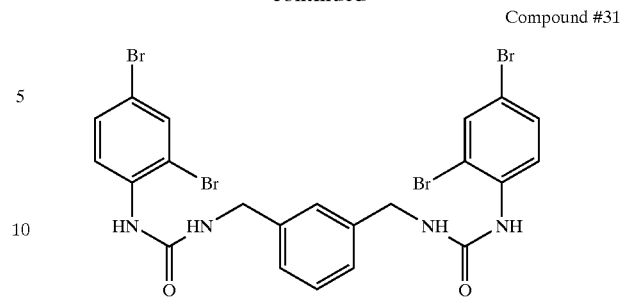

Compound #32

Compound #33
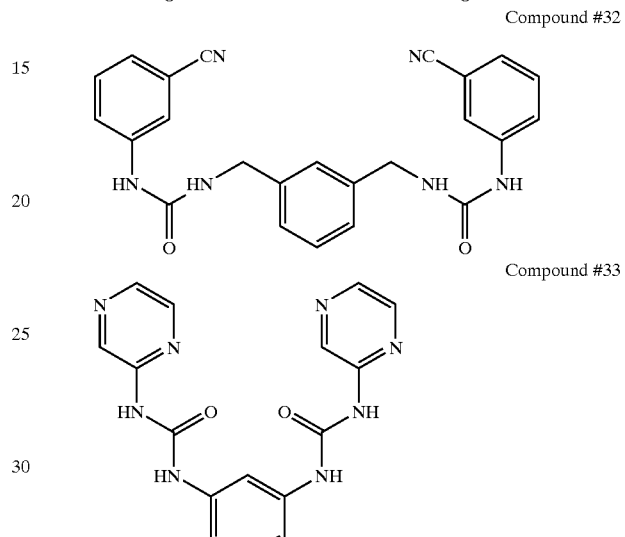

Each of compounds 1–4, 6, 7, and 10–31 significantly inhibit cyclophilin rotamase activity at a concentration of 10 μM or below, and many inhibit 50% of cyclophilin rotamase activity at a concentration lower than 5 μM (IC$_{50}$), some lower than 1 μM. Compounds 6 and 7 possess neurotrophic or neuroprotectant activity.

These data demonstrate the broad range of possibilities for a number of structural elements in the compounds of the invention. Indeed, a number of substituents are well tolerated. Accordingly, the scope of the invention is not limited to those compounds specifically described by Formulae I and II and those depicted in this specification. By performing any one or more of the assays for detecting CyP binding, one skilled in the art can determine whether or not modifications to the R$^{1-5}$ groups, X or Y groups, or the value of n for Formulae I and II, result in a CyP binding compound of this invention.

Preparation of Compounds

The compounds useful in the methods of this invention can be prepared by a number of synthetic routes. The examples below detail schemes 1 to 4 and the preparation of specific compounds. However, one skilled in the art can modify the steps, reactants, and reaction conditions in the examples and schemes to arrive at numerous examples of compounds of the invention. In addition, if particular stereoisomers or mixtures are desired, the starting materials and/or reactants in the preparatory scheme can be selected and used accordingly. Alternatively or in addition, particular intermediates can be purified or enriched by chromatographic or enzymatic methods, or by manipulating reaction conditions or selective crystallization, to generate particular final products or mixtures. One skilled in the art is familiar with numerous methods to selectively produce or enrich for desired stereoisomers or mixtures. All of the compounds of the examples, including the intermediates, are specifically included in the compounds of the invention and can be used in the methods of the invention.

The compounds of the invention may be prepared as a salt or derivative. Various salts and derivatives are known in the art and a non-limiting list of possible choices includes acid salts: acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, mesylate, dimesylate, pamoate, pectinate, persulfate, 3-phenylpropionate, phosphates, picrate, pivalate, propionate, succinate, sulfates, tartrate, thiocyanate, tosylate, and undecanoate. Base salts may include: amine salts, ammonium salts, alkali metal salts such as sodium and potassium salts, alkaline earth metal salts such as calcium and magnesium salts, salts with organic bases such as dicyclohexylamine salts, N-methyl-D-glucosamine, and salts with amino acids, for example arginine or lysine. Nitrogen-containing groups of the compound can be quaternized with agents as: alkyl halides, for example methyl, ethyl, propyl, and butyl chlorides, bromides, or iodides; dialkyl sulfates, for example dimethyl, diethyl, dibutyl and diamyl sulfates, long chain halides, for example decyl, dodecly, lauryl, myristyl, or stearyl chlorides, bromides, or iodides; and aralkyl halides, for example benzyl and phenethyl bromides, chlorides, or iodides. The skilled artisan is familiar with methods for producing and testing any suitable salt or derivative. (See, for example, *Remington's Pharmaceutical Sciences,* Mack Publishing Co., Easton, Pa., 18$^{th}$ Edition, specifically incorporated herein by reference.)

Activity in Neuronal or Nervous System Cells

In general, activity in the nervous system for a particular compound can be identified by assaying for the ability to promote neurite outgrowth, protect neurons from damage by chemical treatments, promote the growth of neurons or neuronal cells, recover lost or damaged motor, functional or cognitive ability associated with nervous tissue or organs of the nervous system, or regenerate neurons. These activities can be useful in treating, diagnosing, or prognosing a number of human disease conditions, including, but not limited to, Parkinson's disease, Alzheimer's disease, amyotrophic lateral sclerosis (ALS), traumatic injury, spinal cord injury, multiple sclerosis, diabetic neuropathy, neuropathy associated with medical treatments such as chemotherapy, ischemia or ischemia-induced injury, stroke, oxygen deprivation, retinopathies, peripheral neuropathies, and neuropathies associated with viral infection.

A number of animal model assays and cell culture assays have been developed and can be relied on for their clinical relevance to disease treatments, including the human diseases noted above. Each of the following references can be used as a source for these assays, and all of them are specifically incorporated herein by reference in their entirety for that purpose: Steiner, et al., *Proc. Natl. Acad. Sci. U.S.A.* 94: 2019–2024 (1997); Hamilton, et al., *Bioorgan. Med. Chem.Lett.* 7:1785–1790 (1997); McMahon, et al., *Curr. Opin. Neurobiol.* 5:616–624 (1995); Gash, et al., *Nature* 380:252–255 (1996); Gerlach, et al., *Eur. J. Pharmacol.— Mol. Pharmacol.* 208:273–286 (1991); Apfel, et al., *Brain Res.* 634:7–12 (1994); Wang, et al., *J. Pharmacol. Exp. Therap.* 282:1084–1093 (1997); Gold, et al., *Exp. Neurol.* 147:269–278 (1997); Hoffer et al., *J. Neural Transm.* [*Suppl.*] 49:1–10 (1997); and Lyons, et al., *PNAS* 91:3191–3195 (1994).

Preferred methods for detecting neuronal activity include a neuroprotective assay, in which a compound is tested for the ability to protect against treatment causing glutamate neurotoxicity. Sensory neuronal cultures (DRG) can also be assayed for neurite outgrowth, an assay for neurotrophic activity. Cultured cells are treated with a compound of the invention and later assayed for the presence of new neurite fibers. Immunohistochemistry can aid in the visualization and quantitation of neurites as compared to control.

The compounds of the invention can also be used to promote the establishment or maintenance of tissue or cell cultures. Similar to the use for promoting neuronal cell growth, the compounds can be added to primary, transformed, or established cell cultures. Particularly in the case of neuronal cells, the compounds can induce growth in culture and extend the culture lifetime of cells.

Binding to CyP and Other Uses

In addition to or in the alternative to the activity in neuronal or nervous system cells and the medical disorders disclosed throughout this specification, the compounds of the invention bind CyP. A recognized method for assessing the affinity of the compound to cyclophilin is the rotamase inhibition assay. For this purpose, the following references are specifically incorporated by reference and can be relied on to make assays of rotamase inhibition: Fischer, et al., *Biomed. Biochem. Acta* 43:1101–1112 (1984); Kofron, et al., *Biochem Chem. Soc.* 114:2670–2675 (1992); Harrison et al., *Biochem.* 29:3813–3816 (1990); Lang et al., *Nature* 329:268–270 (1987); Mucke et al., *Biochem.* 31:7848–7854 (1992); Schonbrunner et al., *J. Biol. Chem.*266:3630–3635 (1991); Hsu et al., *J. Am. Chem. Soc.* 112:6745–6747 (1990); and Justice et al., *Biochem. Biophys. Res. Commun.* 171:445–450 (1990).

Pharmaceutical Formulations and Routes of Administration

The compounds of the invention have utility in pharmacological compositions for the treatment and prevention of various medical conditions or for various in vitro and cell culture treatments. The compounds may have utility in pharmacological compositions for the treatment and prevention of HIV-infection, promotion of hair growth, immunosuppression, mitochondrial disorders, treatment of parasitic infections, treatment of ischemic conditions, conditions associated with optic nerve damage, or traumatic injury to nervous tissue—such as, for example, nerve damage incident to prostate surgery/prostatectomy, which results in erectile dysfunction. The compounds of the invention may be prepared as a salt or derivative, as described above.

A compound of the invention can be administered to an animal or human patient by itself or in pharmaceutical compositions where it is mixed with suitable carriers or excipients, at doses to treat or ameliorate various conditions. The compounds according to the present invention preferably have sufficient stability, potency, selectivity, solubility and availability to be safe and effective in treating diseases, injuries and other abnormal conditions or insults to the central nervous system, the peripheral nerves, and other organs. A therapeutically effective dose refers to that amount of the compound sufficient to effect an activity in a nerve or neuronal cell, to produce a detectable change in a cell or organism, or to treat a disorder in a human or other mammal. The word "treat" in its various grammatical forms as used in relation to the present invention refers to preventing, curing, reversing, attenuating, alleviating, minimizing, suppressing, ameliorating or halting the deleterious effects of a disease state, disease progression, injury, wound, ischemia, disease causative agent (e.g., bacteria, protozoans, parasites, fungi, viruses, viroids and/or prions), surgical procedure or other abnormal or detrimental condition (all of which are collectively referred to as "disorders," as will be appreciated by the person of skill in the art). A "therapeutically effective amount" of a compound according to the invention is an amount that can achieve effective treatment, and such amounts can be determined in accordance with the present teachings by one skilled in the art.

The methods of the present invention comprise (i.) administration of a compound of Formula I or II, where the compound is itself therapeutically active in the treatment of the targeted medical condition, or (ii.) administration of a prodrug of a compound of Formula I or II, wherein such prodrug is any compound which is capable of undergoing metabolic conversion to a compound of Formula I or II following administration, or (iii.) administration of a compound of Formula I or II where the compound is capable of undergoing metabolic conversion to a metabolite following administration, and where the metabolite is therapeutically active in the treatment of the targeted medical condition, or (iv.) administration of a metabolite of a compound of Formula I or II, where the metabolite is therapeutically active in the treatment of the targeted medical condition. Thus, the use of a compound of Formula I or II in the methods of the present invention explicitly includes not only the use of the compound itself, but also the modifications ii, iii, and iv discussed in this paragraph, and all such modifications are explicitly intended to be within the scope of the following claims.

Therapeutically effective doses may be administered alone or as adjunctive therapy in combination with other treatments for the medical conditions within the scope of the methods of this invention, or associated diseases. Techniques for the formulation and administration of the compounds of the instant application are known in the art, and may, for example, be found in *Remington's Pharmaceutical Sciences,* Mack Publishing Co., Easton, Pa., 18$^{th}$ edition (1990).

Suitable routes of administration may, for example, include oral, rectal, transmucosal, buccal, or intestinal administration; parenteral delivery, including intramuscular, subcutaneous, intramedullary injections, as well as intrathecal, direct intraventricular, intravenous, intraperitoneal, intranasal, or intraocular injections, and optionally in a depot or sustained release formulation. Furthermore, one may administer the agent of the present invention in a targeted drug delivery system, for example in a liposome coated with an antibody. The liposomes will be targeted to and taken up selectively by cells expressing the appropriate antigen.

The pharmaceutical compositions of the present invention may be manufactured in a manner that is itself known, e.g., by means of conventional mixing, dissolving, emulsifying, encapsulating, entrapping, or lyophilizing processes. Pharmaceutical compositions for use in accordance with the present invention thus may be formulated in conventional manner using one or more physiologically acceptable carriers comprising excipients and auxiliaries, which facilitate processing of the active compounds into preparations, which can thus be used pharmaceutically.

For injection, the agents of the invention may be formulated in aqueous solutions, preferably in physiologically compatible buffers, such as Hank's solution, Ringer's solution, or physiological saline buffer. For transmucosal or buccal administration, penetrants appropriate to the barrier to be permeated may be used in the formulation. Such penetrants are known in the art.

For oral administration, the compounds can be formulated readily by combining the active compounds with pharmaceutically acceptable carriers, well known to those in the art. Such carriers enable the compounds of the invention to be formulated as tablets, pills, capsules, liquids, quick-dissolving preparations, gels, syrups, slurries, suspensions and the like, for oral ingestion by a patient to be treated. Pharmaceutical preparations for oral use can be obtained as a solid excipient, optionally grinding a resulting mixture, and processing the mixture of granules, after adding suitable auxiliaries, if desired, to obtain tablets. Suitable excipients include, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP).

The pharmaceutical compositions also may comprise suitable solid or gel phase carriers or excipients. Examples of such carriers or excipients include calcium carbonate, calcium phosphate, various sugars, starches, cellulose derivatives, gelatin, and polymers such as polyethylene glycols. If desired, disintegrating agents may be added, such as the cross-linked polyvinyl pyrrolidone, agar, or alginic acid or a salt thereof such as sodium alginate or a number of others disintegrants (see, for example, *Remington's Pharmaceutical Sciences,* Mack Publishing Co., Easton, Pa., 18$^{th}$ edition (1990)).

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, pressurized air, or other suitable gas or mixture. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Pharmaceutical formulations for parenteral administration include aqueous solutions of the active compounds in water-soluble form. Additionally, suspensions or emulsions of the active compounds may be prepared as appropriate oily injection preparations. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, suspensions may also contain suitable stabilizers, or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compounds of the invention may further be formulated in pharmaceutical or cosmetic compositions for topical application to the skin in the form of an aqueous, alcoholic, aqueous/alcoholic or oily solution, or of a dispersion of the lotion or serum type, of an emulsion having a liquid or semi-liquid consistency of the milk type, obtained by dispersion of a fatty phase in an aqueous phase (O/W) or vice versa (W/O), or of a suspension or of an emulsion with a soft consistency of the aqueous or anhydrous gel, foam or cream type, or, alternatively, of microcapsules or microparticles, or of a vesicular dispersion of ionic and/or nonionic type, or may further be administered in the form of an aerosol composition comprising a pressurized propellant agent. Pharmaceutical compositions are distinguished from cosmetic compositions by the concentration or strength of the active ingredient, and the intended use of the composition, as will be appreciated by one skilled in the art. The compounds of the invention can also be formulated into various compositions for hair care and, in particular, shampoos, hair-setting lotions, treating lotions, styling creams or gels, dye compositions (in particular oxidation dyes), optionally in the form of color-enhancing shampoos, hair-restructuring lotions, permanent-wave compositions, and the like. Pharmaceutical or cosmetic compositions comprising compounds of the invention can also contain additives and adjuvants which are conventional in the cosmetics field, such as gelling agents, preservatives, antioxidants, solvents, fragrances, fillers, screening agents, odor absorbers and colorants. The amounts of these different additives and adjuvants are those typically employed in the cosmetics field and range, for example, from 0.01% to 20% of the total weight of the composition, preferably 0.1% to 10%, and more preferably 0.5% to 5%. In addition to one or several compounds of the invention, compositions for topical application may further contain additional agents already known in the art to promote hair growth or to prevent or retard hair loss, such as, without limitation, tocopherol nicotinate, benzyl nicotinate or 2,4-diamino-6-piperidinopyrimidine 3-oxide, or may contain other active agents such as antibacterial agents, antiparasitic agents, antifungal agents, antiviral agents, anti-inflammatory agents, antipruriginous agents, anaesthetic agents, keratolytic agents, antiseborrhoeic agents, antidandruff agents, or antiacne agents. The cosmetic or pharmaceutical compositions according to the invention can be topically applied onto the alopecic areas of the scalp and skin of an individual and optionally maintained in contact for a number of hours and optionally rinsed. It is possible, for example, to apply the composition containing an effective amount of at least one compound of the invention in the evening, to retain the composition in contact overnight and optionally to shampoo in the morning. These applications can be repeated daily for one or a number of months, depending on the particular individuals involved.

Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various suitable sustained-release materials have been established and are well known by those skilled in the art. Sustained-release capsules may, depending on their chemical nature, release the compounds for a few days up to over 100 days, preferably 7–28 days. Depending on the chemical nature and the biological stability of the therapeutic reagent, additional strategies for stabilization may be employed.

Pharmaceutical compositions suitable for use in the present invention include compositions wherein the active ingredients are contained in an effective amount to achieve their intended purpose, to effect a therapeutic benefit, or to effect a detectable change in the function of a cell, tissue, or organ. More specifically, a therapeutically effective amount means an amount effective to prevent the development of or to alleviate the existing symptoms of the subject being treated. Determining the effective amount is well within the capability of those skilled in the art, especially in light of the detailed disclosure provided herein.

Toxicity and therapeutic efficacy of the compounds or compositions can be determined by standard pharmaceutical, pharmacological, and toxicological procedures in cell cultures or experimental animals. For example, numerous methods for determining the $LD_{50}$ (the dose lethal to 50% of the population) and the $ED_{50}$ (the dose therapeutically effective in 50% of the population) exist. The dose ratio between toxic and therapeutic effects is the therapeutic index, which can be expressed as the ratio between $LD_{50}$ and $ED_{50}$. Compounds and compositions exhibiting high therapeutic indices are preferred. The data obtained from cell culture assays or animal studies can be used in formulating a range of dosages for use in humans. (See, for example, Fingl et al., in *The Pharmacological Basis of Therapeutics*, Ch. 1 p. 1 (1975).)

ILLUSTRATIVE EXAMPLES

Synthetic Routes to Production of Exemplary Compounds of the Invention

A subset of the compounds of Formula I may be prepared by reacting isocyanates with amines, as depicted in Scheme 1 below.

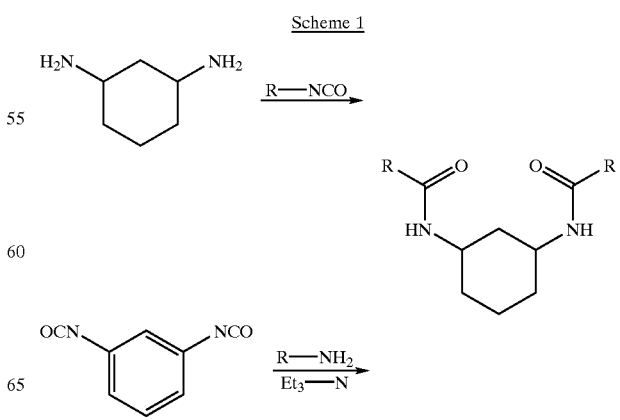

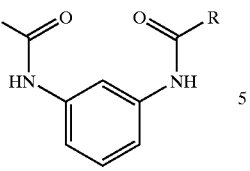

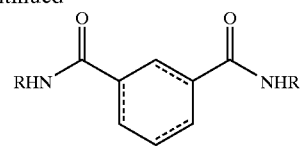

One skilled in the art is familiar with suitable reaction conditions and parameters. The synthesis of compound 9, detailed below, illustrates.

Compound #9

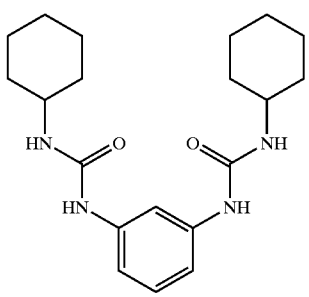

A mixture of phenyl-1,3-diisocyanate (0.1 mmol), cyclohexylamine (0.25 mmol), and diisopropylethylamine (0.1 mmol) in 1 ml dichloromethane was stirred overnight. The resulting precipitate was washed with water and ether to provide (cyclohexylamino)-N-{3-[(cyclohexylamino)carbonylamino]phenyl} formamide (GPI 7104) as a white solid, having $^1$H NMR (CDCl$_3$, 400 MHz) peaks as follows: δ 0.88 (m, 6H); 1.07 (m, 4H); 1.28 (m, 2H); 1.41 (m, 4H); 1.59 (m, 4H); 6.73 (m, 3H); 7.17 (s, 1H); 7.52 (m, 3H); 7.78 (m, 1H).

Another subset of compounds of Formula I may be prepared by the route depicted in Scheme 2 below.

Scheme 2

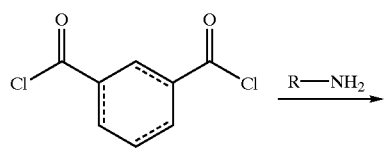

One skilled in the art is familiar with suitable reaction conditions and parameters. The synthesis of compound 14, detailed below, illustrates.

Compound #14

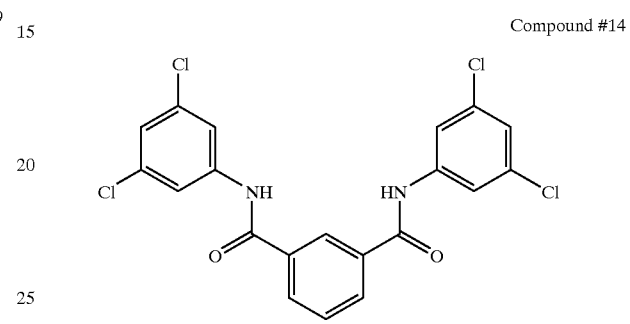

A solution of 1,3-bis-benzoyl chloride (0.99 g, 4.9 mmol), 3,5-dichloroaniline (1.58 g, 9.75 mmol), and triethylamine (2 ml, 14.3 mmol) in 50 ml of dichloromethane was stirred at room temperature overnight. The reaction mixture was washed with water and the resulting precipitated solid was collected by filtration to deliver 1.94 g of crude solid. Recrystallization from acetone furnished analytically pure material with a Mp=260–262° C. and $^1$H NMR (DMSO, 400 MHz) peaks at: δ 7.37 (m, 2H); 7.76 (t, 1H, J=7.8); 7.93 (d, 4H, J=1.8); 8.18 (dd, 2H, J=1.7, 7.8); 8.52 (d, 1H, J=1.5); 10.73 (s, 2H). The theoretical atomic composition for C$_{20}$H$_{12}$N$_2$O$_2$Cl$_4$ [C, 52.90; H, 2.66; N, 6.17; Cl, 31.23], compares favorably with that found experimentally [C, 53.04; H, 2.72; N, 6.11; Cl, 31.35 ].

A subset of the compounds of the invention with unsymmetrical substituents off of the cyclohexyl or phenyl ring structure of Formulae I or II may be prepared by Scheme 3, below.

Scheme 3

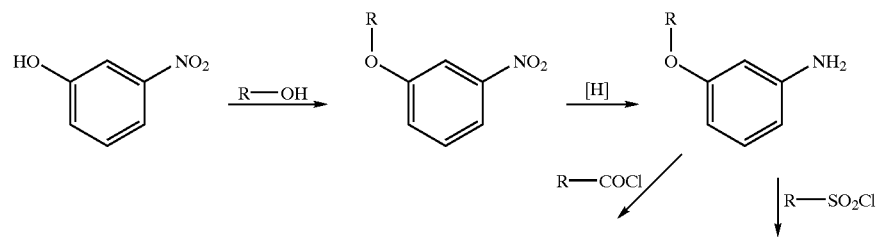

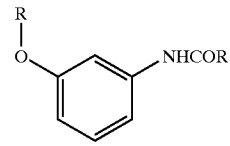 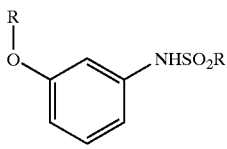

One skilled in the art is familiar with suitable reaction conditions and parameters. The synthesis of compounds 13 and 15, detailed below, illustrates.

Compound #13

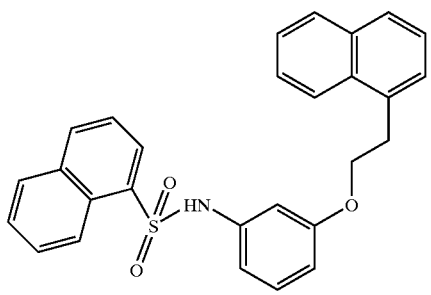

Compound #15

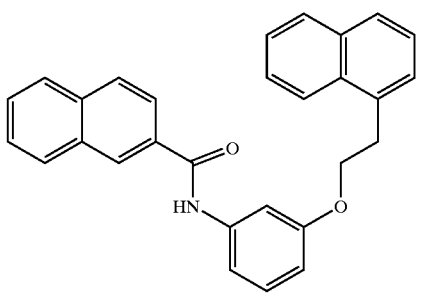

Synthesis of 1-nitro-3-(2-phenylethoxy)benzene.

A stirred solution of 3-nitrophenol (1.39 g, 10 mmol), 1-naphthaleneethanol (1.89 g, 11 mmol), and triphenylphosphine (2.9 g, 11 mmol) in 100 ml of tetrahydrofuran was treated with a solution of 2.22 g (11 mmol) of diisopropylazodicarboxylate added dropwise. The resulting mixture was stirred overnight, and then concentrated and redissolved in a minimum amount of ethyl acetate. Purification on a silica gel column, eluting with 10% ethyl acetate in hexane, delivered 2.0 g of the ether.

Synthesis of 3-(2-phenylethoxy)phenylamine.

To a refluxing suspension of 150 mg "wet" Raney-Nickel in 100 ml of ethanol containing 1.70 g (34 mmol) of hydrazine hydrate was added the nitro compound. After refluxing for an additional 15 minutes, the mixture was cooled and filtered through Celite to remove solids. Removal of the solvent furnished the product as an orange oil, which crystallized on standing and was used without further purification for the next step.

Synthesis of naphthyl-N-[3-(2-naphthylethoxy)phenyl]formamide, compound #15.

A solution of 3-(2-phenylethoxy)phenylamine (200 mg, 0.76 mmol), 1-naphthoyl chloride (160 mg; 0.84 mmol), and triethylamine (0.2 ml, 1.43 mmol) in 50 ml of dimethylacetamide was stirred overnight. The solvent was removed and the residue dissolved in ethyl acetate and washed with water and brine. After concentration, a clear oil was obtained that crystallized on standing. This was purified on a silica gel column, eluting with methylene chloride, to obtain 200 mg of compound #15 as a white solid, Mp=191–193° C., and $^1$H NMR (DMSO, 400 MHz) peaks of: δ 3.56 (t, 2H, J=6.8); 4.31 (t, 2H, J=6.9); 6.71 (dd, 1H, J=2.1, 8.1); 7.25 (t, 1H, J=8.0); 7.34 (bd, 1H, J=8.4); 7.47–8.22 (m, 15H); 10.52 (s, 1H). The theoretical atomic composition for $C_{29}H_{23}NO_2$ [C, 83.43; H, 5.55; N, 3.35] compares favorably to that found experimentally [C, 83.29; H, 5.69; N, 3.39].

Synthesis of [3-(2-naphthylethoxy)phenyl] (naphthylsulfonyl)amine, compound #13.

A solution of 3-(2-phenylethoxy)phenylamine (200 mg, 0.76 mmol), 1-naphthylsulfonyl chloride (190 mg, 0.84 mmol), and triethylamine (0.2 ml, 1.43 mmol) was stirred overnight and worked up as described in the previous example. Purification of the crude product delivered 210 mg of compound 13, Mp=165–167° C., and $^1$H NMR (DMSO, 400 MHz) peaks of: δ 3.42 (t, 2H, J=6.8); 4.10 (t, 2H, J=6.9); 6.48–6.60 (m, 3H); 7.01 (t, 1H, J=8.1); 7.40–8.20 (m, 13H); 8.70 (d, 1H, J=8.6); 10.68 (s, 1H) The theoretical atomic composition for $C_{28}H_{23}NSO_3$ [C, 74.15; H, 5.11; N, 3.09; S, 7.07] compares favorably with that found experimentally [C, 73.88; H, 5.05; N, 3.06; S, 7.03].

Additional examples of compounds of the invention may be prepared as depicted in Scheme 4 below.

Scheme 4

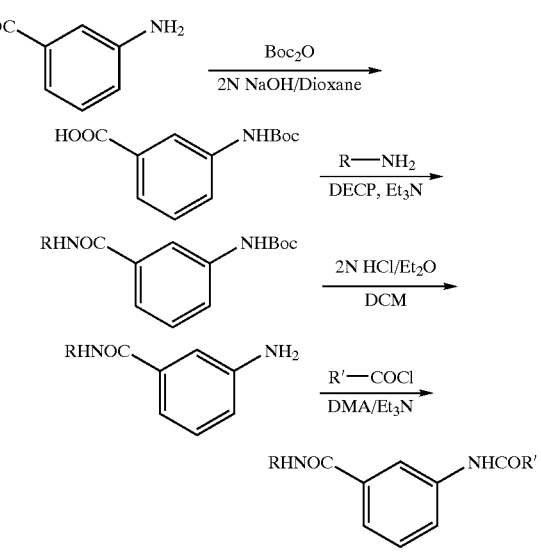

The synthesis of compound 16, detailed below, illustrates.

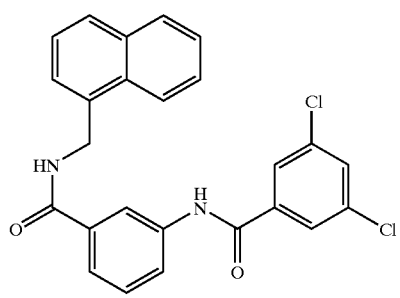

Compound #16

Synthesis of 3-[(tert-butoxy)carbonylamino]benzoic acid.

3-Aminobenzoic acid (5.0 g, 36.5 mmol) was dissolved in 150 ml of 2N NaOH. Dioxane (100 ml) was added, followed by 9.6 g (44 mmol) of tert-butyl dicarbonate added slowly, with stirring. After the addition was complete, the mixture was stirred overnight. It was diluted with water and washed with ether (3 portions). The aqueous phase was acidified with 20% citric acid, and the resulting purplish solid was collected by filtration and recrystallized from ethyl acetate to obtain 1.6 g of the Boc-protected amine.

Synthesis of {3-[(tert-butoxy)carbonylamino]phenyl}-N-(naphthylmethyl)formamide.

A solution of 3-[(tert-butoxy)carbonylamino]benzoic acid (250 mg, 1.05 mmol), 1-naphthylmethylamine (170 mg, 1.05 mmol), diethyl cyanophosphonate (260 mg, 1.6 mmol), and triethylamine (0.22 ml, 1.6 mmol) in acetonitrile was stirred overnight. The solvent was evaporated, and the residue was partitioned between ethyl acetate and 1N HCl. The layers were separated, and the organic phase was washed twice more with 1N HCl, then 3 times each with water and brine. The solvent was removed in vacuo, and the crude product was purified on a silica gel column, eluting with 20% ethyl acetate in hexane, to deliver 270 mg of the amide.

Synthesis of {3-[(3,5-dichlorophenyl)carbonylamino]phenyl}-N-(naphthylmethyl) formamide, Compound 16.

{3-[(tert-Butoxy)carbonylamino]phenyl}-N-(naphthylmethyl) formamide (270 mg, 0.72 mmol) was dissolved in 25 ml of dichloromethane and treated with 7 ml of 2N HCl in ether. After stirring overnight, the precipitate was collected by filtration and dried under vacuum. The aniline (190 mg, 0.61 mmol) was dissolved in dimethylacetamide (10 ml), and 3,5-dichlorobenzoyl chloride (130 mg, 0.61 mmol) and triethylamine (0.5 mL) were added and the resulting mixture was stirred overnight. The product was worked up as described above and recrystallized from ethyl acetate to provide compound 16 as a white crystalline solid, Mp=205–208° C., and $^1$H NMR (DMSO, 400 MHz) peaks of: δ 4.97 (d, 2H, J=5.76); 7.45–8.26 (m, 14H); 9.10 (t, 1H, J=5.76); 10.57 (s, 1H). The theoretical atomic composition for $C_{25}H_{18}N_2O_2Cl_2$ [C, 66.83; H, 4.04; N, 6.23; Cl, 15.78] compares favorably with that found experimentally [C, 66.73; H, 4.15; N, 6.16; Cl, 15.81].

Exemplary Ways to Detect Binding to a CyP
Measuring the Inhibition of Rotamase (prolyl peptidyl cis-trans isomerase) Activity A number of substrates for rotamase are known in the art or can be derived from those known. Typically, the substrate contacts a sample containing a protein with rotamase activity and the conversion of the substrate is detected after a period of time. The method for detecting conversion of the substrate will vary with the particular substrate chosen. One method has been termed the $K_i$ test (See Harding, et al., Nature, 341:758–760 (1989). The cis-trans isomerization of an alanine-proline bond in a model substrate, N-succinyl-Ala-Ala-Pro-Phe-p-nitroanilide, is monitored spectrophotometrically in a chymotrypsin-coupled assay. The action of chymotrypsin releases p-nitroaniline from only the trans form of the substrate. The amount of p-nitroaniline can be monitored in a spectrophotometer, for example. Other methods of detecting the presence of p-nitroaniline can also be used. The inhibition of this reaction caused by different concentrations of inhibitor is determined and the data is analyzed as a change in first-order rate constant as a function of inhibitor concentration, which yield the $K_i$ value.

The following were added to a plastic cuvette: 950 mL of ice cold assay buffer (25 mM HEPES, pH 7.8, 100 mM NaCl), 10 μL of CyP A (2.5 μM in 10 mM Tris-Cl pH 7.5, 100 mM NaCl, 1 mM dithiothreitol), 25 μL of chymotrypsin (50 mg/ml in 1 mM HCl), and 10 μL of test compound, at various concentrations, in dimethyl sulfoxide. The reaction was initiated by the addition of 5 μL of substrate (succinyl-Ala-Phe-Pro-Phe-para-nitroanilide, 5 mg/mL in 470 mM LiCl in trifluoroethanol). The absorbance at 390 nm versus time was monitored for 90 seconds using a spectrophotometer.

The inhibition values obtained for representative compounds are listed in the following Table I, and refer to the percent of rotamase activity that is inhibited by the compound when the compound is present at a concentration of 10 μM. The higher the percentage, the more the compound inhibits rotamase, which in turn means the more active the compound is at binding or interacting with CyP. The $IC_{50}$ values refer to the concentration that inhibits 50% of the rotamase activity in a sample. The lower the value, the more active the compound is at binding or interacting with CyP. While CyP A is used in these examples, other CyP proteins can be substituted. Similar methods can be used with other immunophilins, such as the FKBPs, to demonstrate the presence or absence of FKBP binding activity. Preferred compounds have an $IC_{50} \leq 1$ μM for inhibition cyclophilin rotamase activity, more preferably ≦500 nM, and most preferably ≦100 nM. Especially preferred compounds, because of their selectivity, may also have an $IC_{50} \geq 10$ μM, or ≧50 μM, for inhibition of FKBP rotamase activity.

TABLE I

| Compd | % Inhibition at 10 μM | $IC_{50}$ (μM) | Compd | % Inhibition at 10 μM | $IC_{50}$ (μM) |
| --- | --- | --- | --- | --- | --- |
| 1 | 100 | 6 | 19 | 98 | 2.9 |
| 3 | 100 | 0.6 | 20 | 100 | 4.85 |
| 4 | 100 | 0.80 | 21 | 100 | 1.92 |
| 6 | 100 | 1.02 | 22 | 100 | 8.2 |
| 7 | 100 | 1.9 | 23 | 100 | 4.2 |
| 10 | 99 | 4.5 | 24 | 100 | 5.09 |
| 11 | 93 | 4.0 | 25 | 100 | 3.25 |
| 12 | 47.7 | 9.5 | 26 | 100 | 5.64 |
| 13 | 100 | 0.83 | 27 | 100 | 8.55 |
| 14 | 100 | 0.97 | 28 | 100 | 2.95 |
| 15 | 100 | 0.74 | 29 | 89 | 6.2 |
| 16 | 100 | 1.0 | 30 | 88 | 3.95 |
| 17 | 99 | 0.65 | 31 | 100 | 3.9 |
| 18 | 100 | 0.52 | 32 | n.d. | — |
|  |  |  | 33 | 2 |  |

Neuroprotection Assay

Protection of cells from calcium-related physiological stress can be assessed in a neuroprotection assay. Organotypic slice cultures of rat spinal cord tissue display a protracted loss of ventral horn motoneurons when exposed to the glutamate uptake inhibitor THA. All cultures were derived from postnatal day 8 (P8) Sprague-Dawley rat lumbar spinal cord slices of 325 micron thickness. Each experiment consisted of two 6-well plates with 5 slices from 4 different animals per well. Media changes were performed every 3 to 4 days. Cultures were treated with THA [L(-)-threo-3-hydroxyaspartic acid; Tocris Cookson Inc., Ballwin, Mo.] at 200 µM+compound (10 µM) after one week in culture. The control was an untreated sample with 0.1% DMSO as vehicle. The THA control was a THA treated sample with 0.1% DSMO as vehicle. Two wells were used per condition. One media change with new THA and compounds was performed. The experiment was stopped 6 to 8 days following drug treatment (13–15 total days in vitro, DIV) as dictated by visual assessment of lesion, by fixation with 4% paraformaldehyde/0.1 M phosphate buffer for 30 minutes. Slices were permeabilized with 100% cold methanol for 10 minutes. Slices were transferred to staining wells. The slices were blocked with 10% horse serum/TBS. Primary antibody incubation was overnight at 4° C. with SMI-32 antibody 1:5000 in 2% horse serum/TBS. SMI-32 is specific towards the unphosphorylated H neurofilament subunit, and was here utilized as a marker for ventral horn motoneurons. A Vectastain ABC Elite Kit with rat absorbed anti-mouse secondary antibody was used with DAB to stain the slices. The slices were mounted under DPX mounting solution for microscopy.

Figure 2:
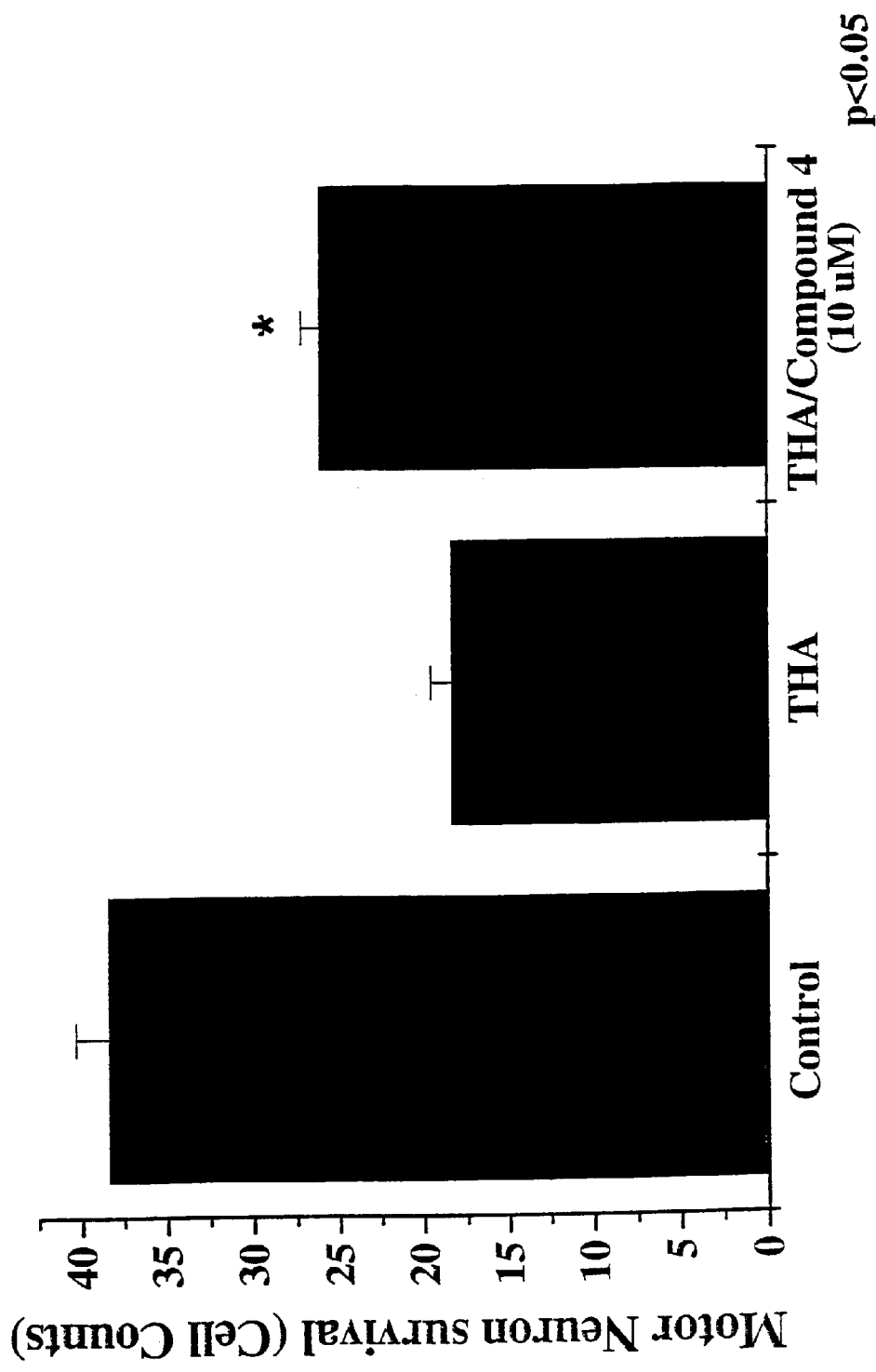
FIG. 2: An experiment as discussed in FIG. 1, where compound #4 was used. Compound #4 also displays neuroprotective activity.
Figure 3:
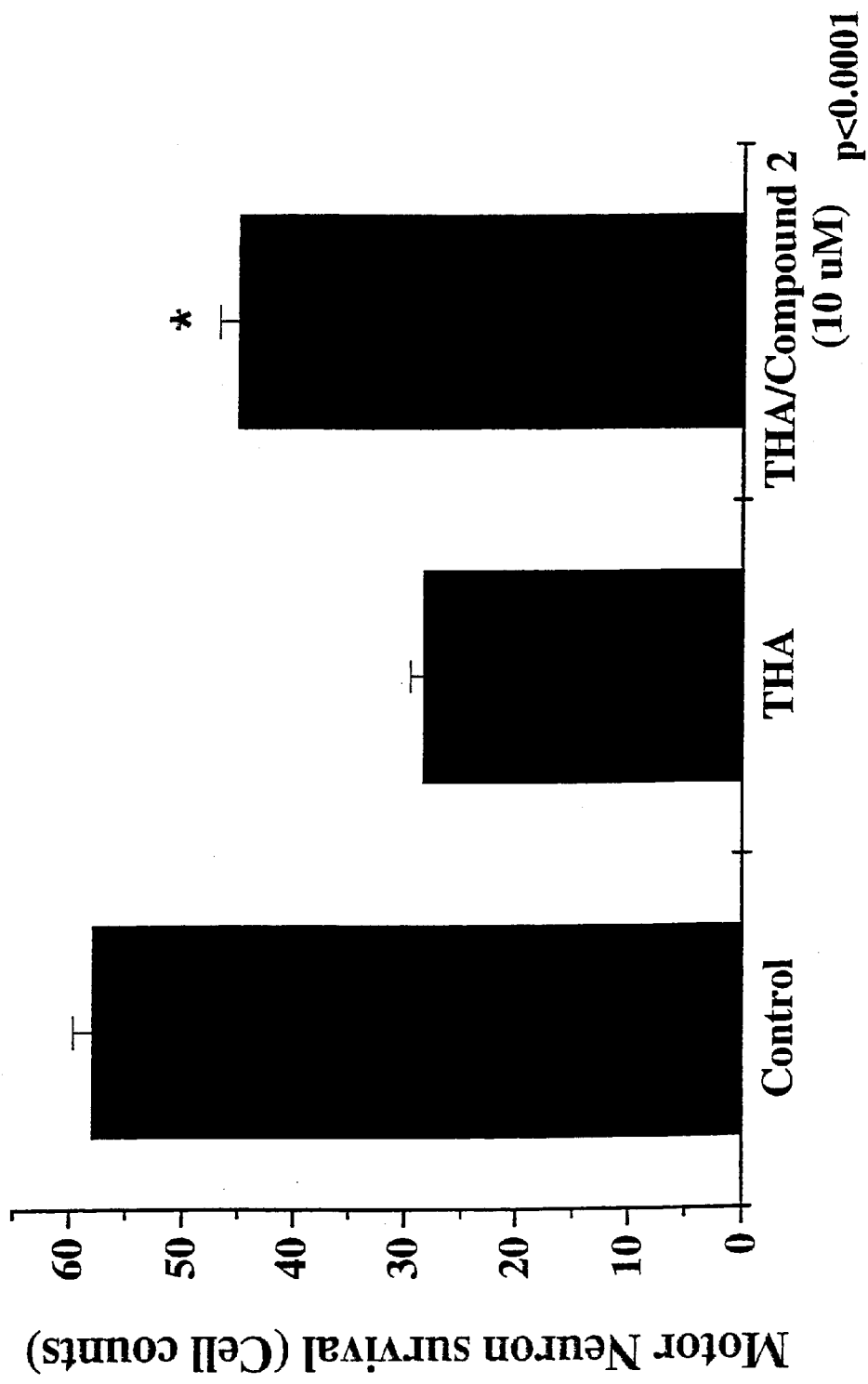
FIG. 3: An experiment as discussed in FIG. 1, where compound #2 was used. Compound #2 also displays neuroprotective activity.
Figure 4:
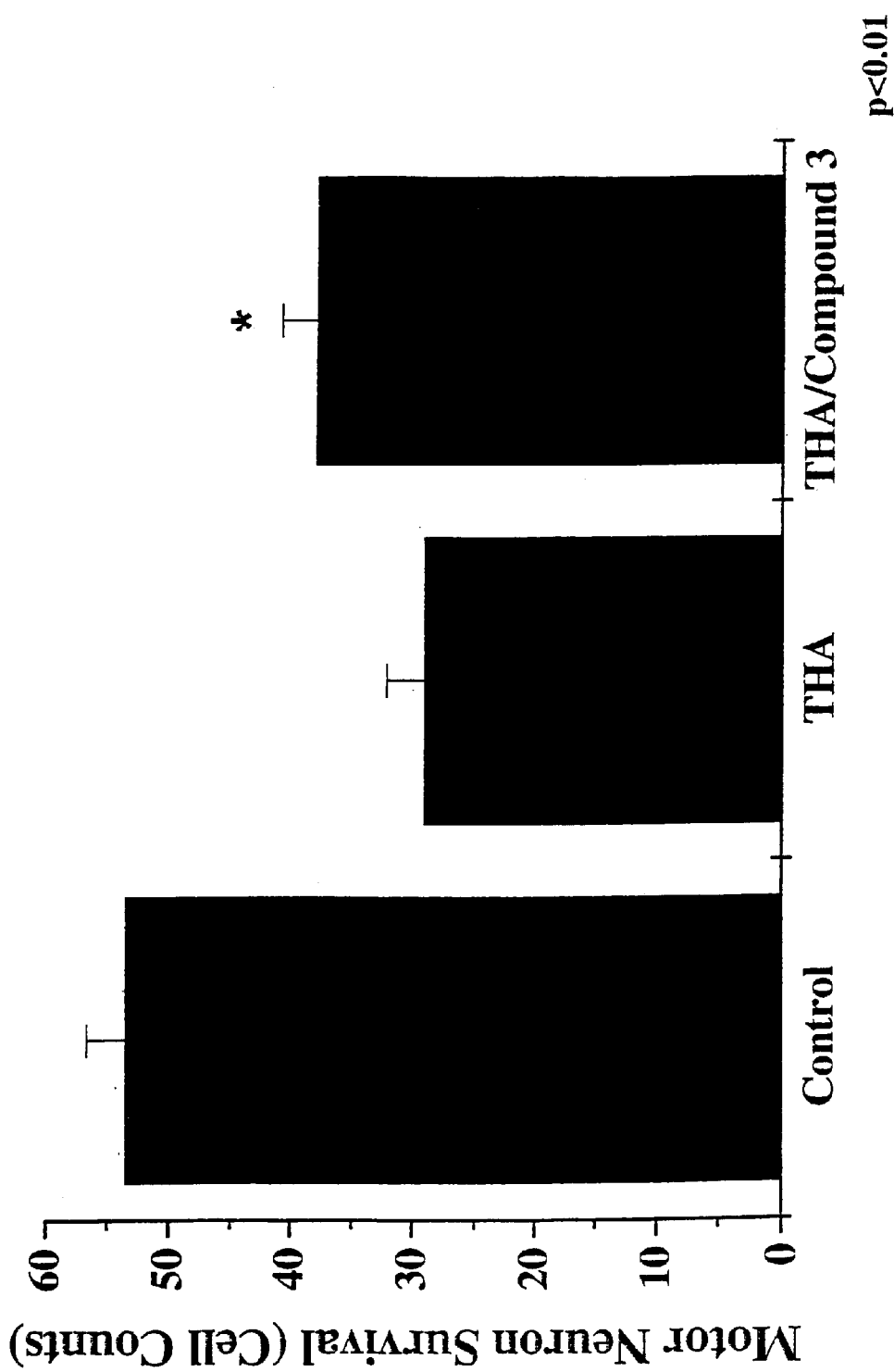
FIG. 4: An experiment as discussed in FIG. 1, where compound #3 was used. Compound #3 also displays neuroprotective activity.
Figure 5:
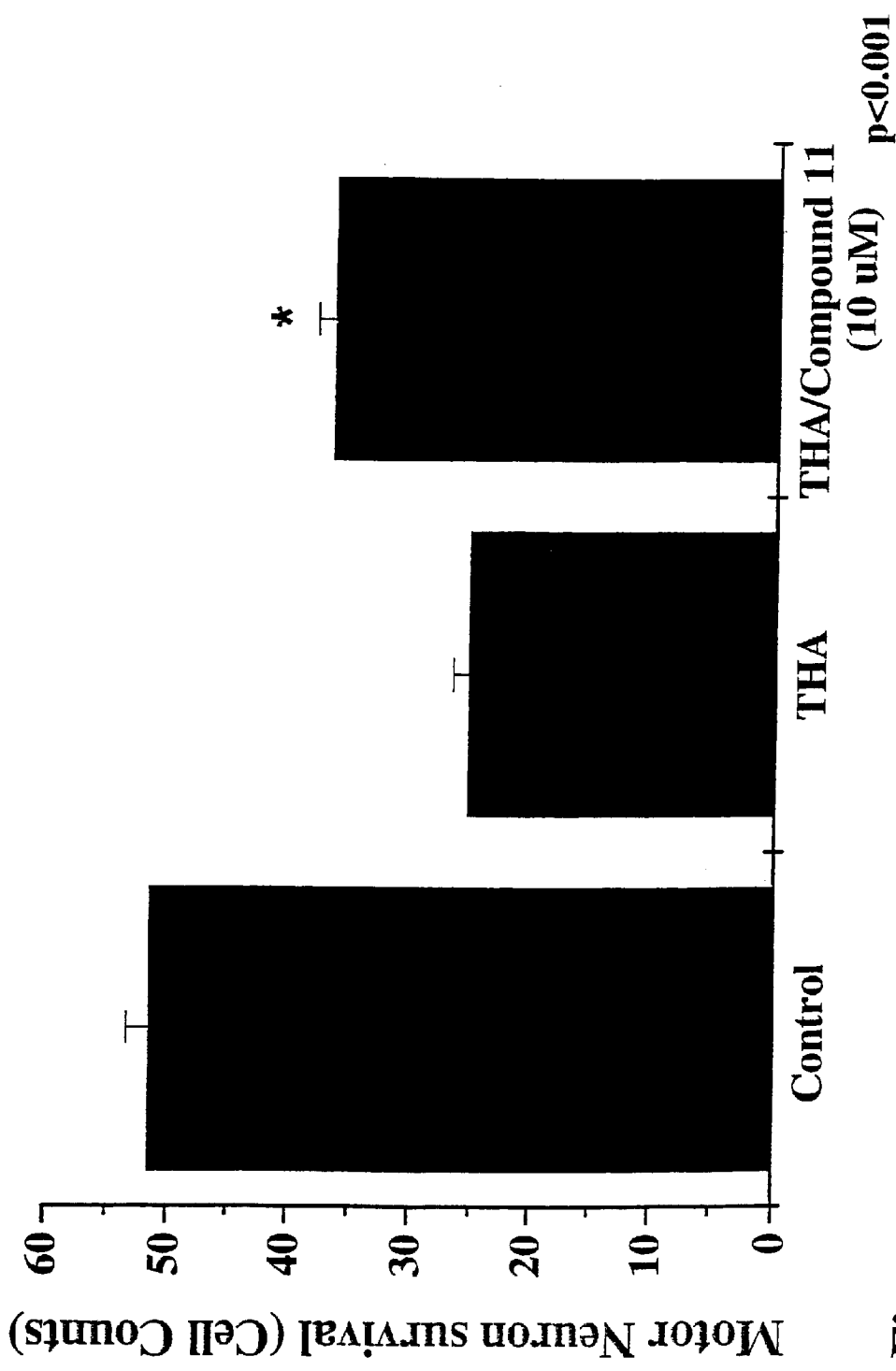
FIG. 5: An experiment as discussed in FIG. 1, where compound #11 was used. Compound #11 also displays neuroprotective activity.
Figure 6:
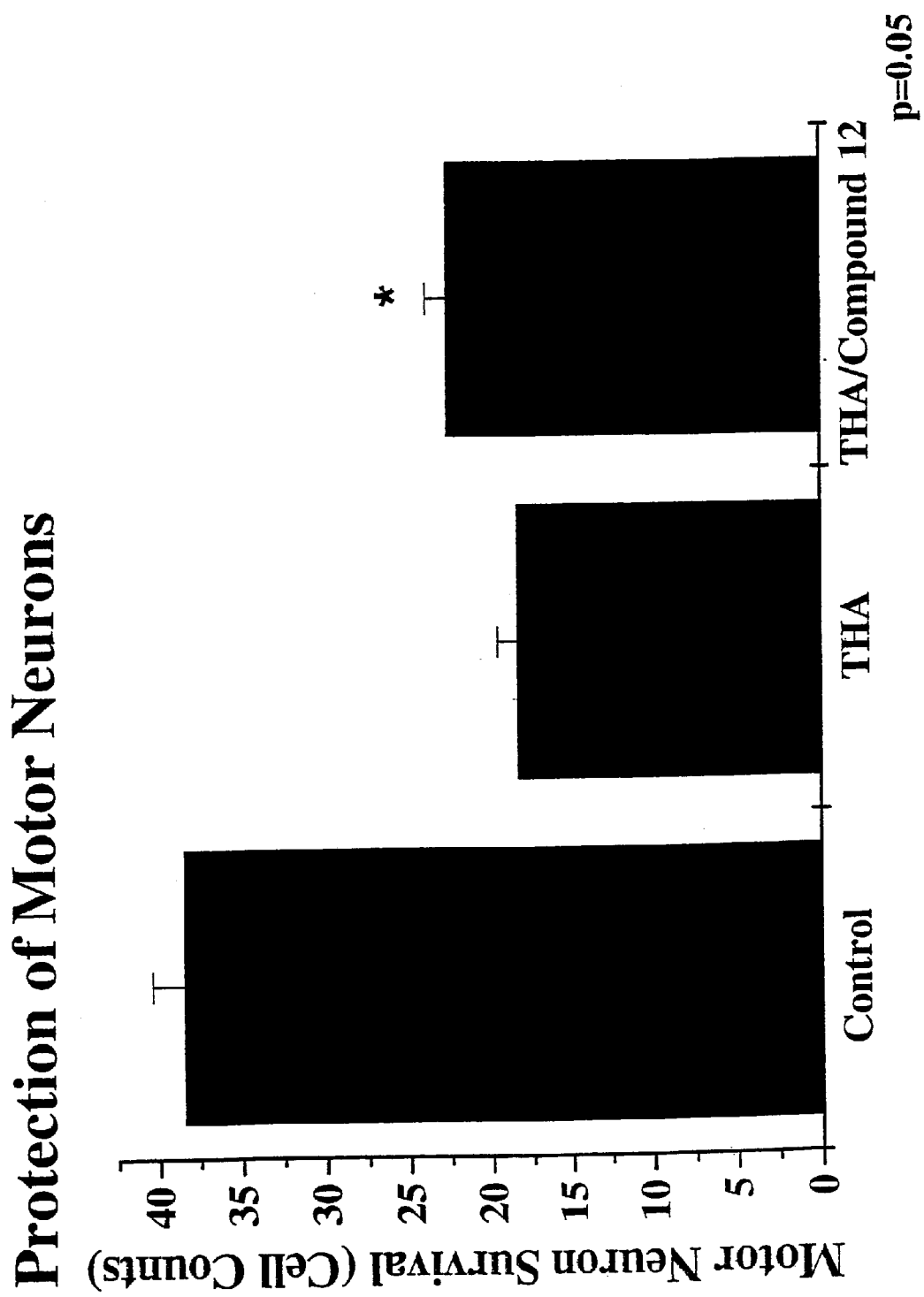
FIG. 6: An experiment as discussed in FIG. 1, where compound #12 was used. Compound #12 also displays neuroprotective activity.

Quantification of surviving neurons was performed on a Zeiss Axiovert microscope. Neuronal survival was determined by observing an intact neuronal cell body with processes located ventrally of the central canal in each hemisphere. This correlated to laminae VII, VIII and IX. Each hemisphere was counted individually. The statistics were performed with StatView software on a minimum of three different experiments per condition and significance was determined as compared to THA control. The percent of protection was determined from the average number of living neurons by the following equation: (drug treatment condition —THA control)/(Untreated control-THA control). Typical results are shown in FIGS. 1–6.

Inhibition of Mitochondrial Permeability Transition in a Spectrophotometric Large Amplitude Mitochondrial Swelling Assay Fresh rat liver mitochondria are prepared from male Sprague-Dawley rats as described by Broekemeier, et al., *J. Biol. Chem.* 260:105–113 (1985). Incubations are conducted at room temperature in an assay buffer containing 10 mM sodium succinate, 3 mM Hepes (pH 7.4), 5 µM rotenone, 0.5 µg/ml oligomycin, 10 µM $CaCl_2$, and mannitol/sucrose at a ratio of 3:1 to yield an osmotic strength of 300 mosmoles. Five µl of the isolated mitochondria preparation and 5 µl of compound or vehicle solution are added at various concentrations and optical density (OD) is read at 540 nm for one minute to obtain a baseline reading. Ten µl of ruthenium red solution is added to yield a final concentration of 1 µM, and $OD_{540}$ is monitored for an additional minute. Twenty-five µl of fluoro-carbonyl cyanide solution is added to yield a final concentration of 4 µM, and $OD_{540}$ is monitored for an additional 4–5 minutes. Mitochondrial permeability transition is manifested as a progressive drop in net absorbance as the mitochondria swell. The ability of the compounds of Formulae I or II to inhibit mitochondrial permeability transition and swelling can be expressed as $IC_{50}$ values. Compounds of Formulae I or II significantly inhibit the progressive drop of net absorbance at $OD_{540}$, and inhibit the mitochondrial permeability transition in a dose-dependent manner.

In Vivo Protective Effects in an Animal Model of Cerebral Stroke

Male Sprague Dawley rats, weighing 260–290 g, are used in determining the protective effects of the compounds of the invention against ischemia-induced brain damage. The compounds are dissolved in 50 mM Hepes buffered saline or another physiologically acceptable vehicle, and the pH is adjusted to 7.4 before administration. The compound is administered intravenously 60 min following experimental medial cerebral artery occlusion (MCAO) at a bolus dose of, e.g., 100 mg/kg immediately followed by an infusion dose of 20 mg/kg/hr for 4 hours. MCAO surgery: The intraluminal filament model of transient MCAO is well established in the art [see, e.g., Lu, et al., *Eur. J. Pharmacol.* 408: 233–239 (2000)]. Briefly, under 1.5% halothane anesthesia, the rat common carotid artery is exposed at the level of external and internal carotid artery bifurcation. The external carotid artery (ECA) and its branches are cauterized and cut. A piece of 3–0 monofilament nylon suture with a blunted tip is introduced into the internal carotid artery (ICA) via the proximal end of the ECA stump. The suture is advanced through the carotid canal to the origin of the MCA where it blocks the blood flow to its entire territory. At the end of the 2 hour occlusion period, the rat is re-anesthetized and the suture is carefully pulled back to the ECA stump to allow reperfusion. During the surgery, the animal's body temperature is maintained at 37.0° C. via a heating blanket. The experimental animals are sacrificed following 22 hr of reperfusion. The brains are removed and cut into seven 2-mm thick coronal slices, stained with 1% 2,3,5-triphenytetrazolium chloride (TTC), and subsequently imaged using a computer-assisted digital imaging analysis system. The ischemic injury is quantified based on the volume of the infarct tissue completely lacking TTC staining. The total infarct volume and the infarct volumes of the cortical and subcortical regions of each rat are used for statistical analysis. A one-factor analysis of variance can be used for comparison of treatment effects. The difference between groups is considered statistically significant at $p<0.05$. Administration of compounds of Formulae I or II lead to a significant reduction in infarct volume as compared to vehicle-treated animals.

In Vivo Protective Effects in an Animal Model of Myocardial Infarction

The surgical procedure and protocol for inducing experimental myocardial infarction is itself well-established in the art [see, e.g., Kukreja, et al. , *Mol. Cell. Biochem.,* 195: 123–131 (1999)]. Briefly, male Sprague-Dawley rats (225–300 g) are anaesthetized with 65 mg/kg sodium pentobarbital i.p;. Following tracheotomy, animals are mechanically ventilated using 35% $O_2$/65% $N_2$ at 50 strokes/min. and a stroke volume of 2 ml, and maintained at 37.0° C. using a heating blanket. Electrocardiographic leads are attached to subcutaneous electrodes to monitor either limb leads I, II or III. The right carotid artery is cannulated and connected to a pressure transducer to monitor arterial pressure throughout the experiment, and the right jugular vein is cannulated to allow intravenous administration of compounds of the invention. The compounds are dissolved in 50 mM Hepes buffered saline or another physiologically acceptable vehicle, and the pH is adjusted to 7.4 before administration. The compound is administered intravenously 20 min prior to experimental coronary artery occlusion at a bolus dose of, e.g., 100 mg/kg, immediately followed by an infusion dose of 20 mg/kg/hr for 140 minutes. A left thoracotomy is performed at the fourth intercostal space and the heart exposed. A 5–0 silk suture with a traumatic needle is then passed around the left coronary artery midway between the atrioventricular groove and the apex, and the ends of the suture thread are passed through a piece of vinyl tubing to form a snare. The coronary artery is transiently occluded by tightening and fixing the snare. Myocardial ischemia can be confirmed visually by regional cyanosis of the exposed heart, hypokinetic movement of the heart muscle, or by ST segment elevation/depression or T wave inversion on the electrocardiogram. The snare is released after 30 minutes and reperfusion is visually confirmed by hyperemia over the previously cyanotic area of the heart muscle, and by hemodynamic improvement in blood pressure. Following 90 minutes of reperfusion, the snare is again tightened and approximately 1 ml of Evan's blue dye is injected as a bolus vial the jugular vein catheter. The animals are sacrificed immediately, the hearts are removed, frozen, and cut from apex to base into 6–8 transverse 2 mm-thick slabs. The area at risk is determined by the absence of Evan's blue staining. The slices are then incubated in 1% TTC solution for visualization of viable tissue. The infarct volume and area at risk are quantitated using a commercially available image analysis system. Administration of compounds of Formulae I or II leads to a significant dose-dependent reduction in infarct volume as compared to animals treated with vehicle alone.

In Vivo Hair Generation

Experimental methods useful in assessing the ability of the present compounds to protect from cancer chemotherapy-induced alopecia are themselves established in the art. See, e.g., Maurer, et al. *Am. J. Pathol.* 150(4):1433–41 (1997). In addition, a useful experimental model for assessing the ability of compounds to induce hair growth in bald human scalp from subjects with male pattern baldness has been reported. Sintov, et al., *Int. J. Pharm.* 194:125–134 (2000). Simple procedures for the assessment of hair revitalizing properties of experimental compounds have been disclosed previously by the inventors. See, e.g., U.S. Pat. No. 6,194,440 B1. These and other publications referenced herein can be relied upon to assess the hair growth-promoting and hair loss-retarding properties of compounds of Formulae I or II. The following procedure illustrates:

Mice of the C57B1/6 strain, aged 7–8 weeks, are housed individually. Under light ether anaesthesia, an area of about 2 cm by 2 cm of the lower back/hindquarter region is shaved to remove all existing hair. Care is taken to avoid scrapes, cuts or abrasions of the skin. A pinkish color of the skin confirms that all animals are in the telogen phase of the hair growth cycle. Groups of 10 animals are treated topically with 20% propylene glycol vehicle, or with compounds of the invention at concentrations ranging from 0.1 $\mu$M to 100 $\mu$M per milliliter vehicle. Compounds are topically administered three times per week, and hair growth is assessed weekly by a blinded observer on a scale of 0 (no growth) to 5 (complete hair growth over shaved area). The compounds of the invention induce the growth of hair in a dose-dependent manner, and significantly shorten the time elapsed until the shaved area is covered by hair, as compared to the shaved area of vehicle-treated animals.

As noted above, the specific examples should not be interpreted as a limitation to the scope of the invention. Instead, they are merely exemplary embodiments one skilled in the art would understand from the entire disclosure of this invention.

References Cited

Each of the references cited below or in the text above can be relied on to make and use any aspect of this invention. While particular uses and references are discussed above, this should not be taken as a limitation on the use of any particular reference. All the references are specifically included into this text by reference, in their entirety.

Apfel, et al., *Brain Res.* 634: 7–12 (1994);
Ausubel, et al., eds., *Current Protocols in Molecular Biology*, John Wiley & Sons, N.Y., (and supplements through December 2000);
Bell, et al., *Biochem. Pharmacol.* 48:495–503 (1994);
Berriman and Fairlamb, *Biochem. J.* 334:437–445 (1998);
Broekemeier, et al., *J. Biol. Chem.* 264: 7826–7830 (1989);
Coligan, et al., eds., *Current Protocols in Immunology*, John Wiley and Sons, N.Y., (and supplements through December 2000);
Enna, et al., eds., *Current Protocols in Pharmacology*, John Wiley & Sons, N.Y., (and supplements through December 2000);
Fingl, et al., in *The Pharmacological Basis of Therapeutics*, Ch. 1, (1975);
Fischer, et al., *Biomed. Biochem. Acta* 43: 1101–1112 (1984);
Friedman et al., *Proc. Natl. Acad. Sci.*, 90:6815–6819 (1993);
Gash, et al., *Nature* 380: 252–255 (1996);
Gerlach, et al., *Eur. J. Pharmacol.—Mol. Pharmacol.* 208: 273–286 (1991);
Gold, et al., *Exp. Neurol.* 147: 269–278 (1997);
Gold, *Mol. Neurobiol.* 15: 285–306 (1997);
Griffiths and Halestrap, *J. Mol. Cell Cardiol.* 25: 1461–1469 (1993);
Hamilton and Steiner, *J. Med. Chem.* 41: 5119–5143 (1998);
Hamilton, et al., *Bioorgan. Med. Chem.Lett.* 7: 1785–1790 (1997);
Handschumacher, et al., *Science* 226:544 (1984);
Harrison, et al., *Biochem.* 29: 3813–3816 (1990);
Harding, et al., *Nature*, 341:758–760 (1989);
Hoffer et al., *J. Neural Transm.* [*Suppl.*] 49:1–10 (1997);
Holt, et al., *Bioorg. Med. Chem. Letters*, 4: 315–320 (1994);
Hsu, et al., *J. Am. Chem. Soc.* 112: 6745–6747 (1990);
Iwabuchi, et al., *J. Dermatol. Sci.* 9: 64–69 (1995);
Jiang, et al., *J. Invest. Dermatol.*, 104 523–525 (1995);
Justice, et al., *Biochem. Biophys. Res. Commun.* 171: 445–450 (1990);
Khattab, et al., *Exp. Parasitol.* 90:103–109 (1998);
Kofron, et al., *Biochem.* 30: 6127–6134 (1991);
Kofron, et al., *J. Am. Chem. Soc.* 114: 2670–2675 (1992);
Kukreja, et al., *Mol. Cell. Biochem.*, 195: 123–131 (1999);
Küllertz, et al., *Clin. Chem.* 44: 502–508 (1998);
Lang, et al., *Nature* 329: 268–270 (1987);
Leducq, et al., *Biochem. J.* 336: 501–506 (1998);
Lemasters, et al., *Mol. Cell. Biochem.* 174: 159–165 (1997);
Li, et al., *J. Med. Chem.* 43: 1770–9 (2000);
Lu, et al., *Eur. J. Pharmacol.* 408: 233–239 (2000);
Lyons, et al., *Proc. Natl. Acad. Sci. U.S.A.* 91:3191–3195 (1994);
Marchetti, et al., *J. Exp. Med.* 184: 1155–1160 (1996);
Matsumoto, et al., *J. Cereb. Blood Flow Metab.* 19: 736–41 (1999);
Maurer, et al. *Am. J. Pathol.* 150(4):1433–41 (1997);
McLauchlan, et al., *Parasitology* 121:661–70 (2000);
McMahon, et al., *Curr. Opin. Neurobiol.* 5: 616–624 (1995);
Mucke, et al., *Biochem.* 31: 7848–7854 (1992);
Palacios, *J. Immunol.* 128:337 (1982);
Paus, et al., *Am. J. Pathol.* 144: 719–34 (1994);
Perkins, et al., *Antimicrob. Agents Chemother.* 42: 843–848 (1998);
*Remington's Pharmaceutical Sciences*, Mack Publishing Co., Easton, Pa., 18th edition (1990);

Sintov, et al., *Int. J. Pharm.* 194:125–134 (2000);
Snyder, *Nat. Med.* 1:32–37 (1995);
Schonbrunner, et al., *J. Biol. Chem.* 266: 3630–3635 (1991);
Steiner, et al., *Proc. Natl. Acad. Sci. U.S.A.* 94: 2019–2024 (1997);
Streblow, et al., *Virology* 245: 197–202 (1998);
Wang, et al., *J. Pharmacol. Exp. Therap.* 282: 1084–1093 (1997);
Yamamoto, et al., *J. Invest. Dermatol.* 102 (1994) 160–164;
Yoo, et al., *J. Mol. Biol.*, 269: 780–795 (1997);
Zahner and Schultheiss, *J. Helminthol.* 61:282–90 (1987); and
Zamzami, et al., *FEBS Lett.* 384: 53–57 (1996).

We claim:

1. A method of treatment or prophylaxis of a non-neurologic ischemic injury or ischemia/reperfusion injury in a mammal is need thereof, comprising administering to said mammal an effective amount of a compound of Formula I,

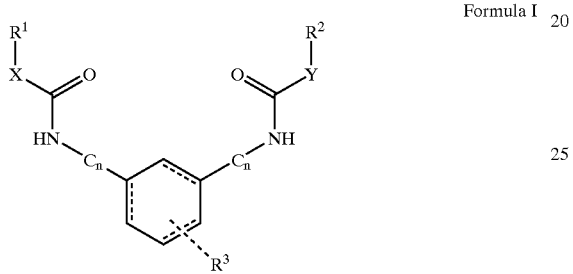

Formula I

Where n in $C_n$ is 0 or 1;
The dashed bond symbol represents an optional bond;
X and Y may independently be N, NH, O, S, or a direct bond;
$R_1$ is the same as or different than $R_2$, and can either be one or more C1–C6 branched or straight chain alkyl or alkenyl groups;
one or more C1–C3 branched or straight chain alkyl groups substituted by one or more Q groups
or one or more Q groups,
where Q, which is optionally saturated, partially saturated, or aromatic, is a mono-, bi-, or tricyclic, carbo- or heterocyclic ring, wherein each ring may be optionally substituted in one to five positions with halo, hydroxyl, nitro, trifluoromethyl, acetyl, aminocarbonyl, methylsulfonyl, oxo, cyano, carboxy, C1–C6 straight or branched chain alkyl or alkenyl, C1–C4 alkoxy, C1–C4 alkenyloxy, phenoxy, benzyloxy, amino, or a combination thereof, and wherein the individual ring sizes are 5–6 members, and wherein each heterocyclic ring contains 1–6 heteroatoms selected from the group consisting of O, N, S, or a combination thereof;
and $R_3$ may be one to three substitutents chosen from the group consisting of halo, hydroxyl, nitro, trifluoromethyl, C1–C4 straight or branched chain alkyl or alkenyl, C1–C4 alkoxy, C1–C4 alkenyloxy, phenoxy, benzyloxy, amino, Q as defined above, or a combination thereof;
wherein said ischemic injury or ischemia/reperfusion injury is selected from the group consisting of mesenteric infarction, bowel ischemia, hepatic infarction, renal infarction, splenic infarction, and ischemic heart disease.

2. The method of claim 1, wherein said ischemic heart disease is congestive heart failure, myocardial ischemia, or coronary heart disease.

* * * * *